(12) United States Patent
Fujita et al.

(10) Patent No.: US 8,980,264 B2
(45) Date of Patent: Mar. 17, 2015

(54) MOUSE ANTI-AGGRUS MONOCLONAL ANTIBODIES

(75) Inventors: Naoya Fujita, Tokyo (JP); Yuya Nakazawa, Tokyo (JP); Satoshi Takagi, Tokyo (JP)

(73) Assignees: Japanese Foundation for Cancer Research, Tokyo (JP); LSIP, LLC, Tokyo (JP)

( * ) Notice: Subject to any disclaimer, the term of this patent is extended or adjusted under 35 U.S.C. 154(b) by 0 days.

(21) Appl. No.: 14/006,498

(22) PCT Filed: Mar. 9, 2012

(86) PCT No.: PCT/JP2012/056142
§ 371 (c)(1),
(2), (4) Date: Sep. 20, 2013

(87) PCT Pub. No.: WO2012/128082
PCT Pub. Date: Sep. 27, 2012

(65) Prior Publication Data
US 2014/0235827 A1    Aug. 21, 2014

(30) Foreign Application Priority Data

Mar. 22, 2011    (JP) ................... 2011-062686

(51) Int. Cl.
*C07K 16/00* (2006.01)
*C07K 16/28* (2006.01)
*C07K 16/30* (2006.01)
*C12N 5/16* (2006.01)

(52) U.S. Cl.
CPC .............. *C07K 16/28* (2013.01); *C07K 16/30* (2013.01); *C12N 5/163* (2013.01); *C07K 2317/24* (2013.01)
USPC ................ 424/133.1; 424/138.1; 530/387.3

(58) Field of Classification Search
None
See application file for complete search history.

(56) References Cited

U.S. PATENT DOCUMENTS

2008/0176851 A1*  7/2008  Kajiya et al. ............... 514/236.8
2008/0317723 A1* 12/2008  Alitalo et al. ............... 424/93.21
2014/0037655 A1*  2/2014  Luo et al. .................... 424/174.1

FOREIGN PATENT DOCUMENTS

WO    2011/040565      4/2011
WO    2012075490   *  6/2012

OTHER PUBLICATIONS

Campbell, Monoclonal Antibody Technology, Elseivers Chapter 1, 1984.*
International Search Report filed in PCT/JP2012/056142.
Kato, Yukinari, et al; "Inhibition of tumor cell-induced platelet aggregation using a novel anti-podoplanin antibody reacting with its platelet-aggregation-stimulating domain", Biochemical and Biophysical Research Communications, 2006, vol. 349, p. 1301-1307.
Kato, Yukinari, et al; "Molecular analysis of the pathophysiological binding of the platelet aggregation-inducing factor podoplanin of the C-type lectin-like receptor CLEC-2", Cancer Sci., 2008, vol. 99, No. 1, p. 54-61.
Kato, Yukinari, et al; "1. Tosa Kino no Kaimei to Tosa Kanren Biomarker no Kaihatsu 4) Kesshoban Gyoshu Inshi Podoplanin no Bunshi Seibutsugakuteki Kaiseki", Gene & medicine MOOK11 RinshoTosa Biomarker no Kaihatsu-Tosa Kino no Kaimei to sono Oyo, 2008, pp. 165-171.
Ogasawara, Satoshi, et al; Characterization of Anti-podoplanin Monoclonal Antibodies: Critical Epitopes for Neutralizing the Interaction Between Podoplanin and CLEC-2, Hybridoma, 2008, vol. 27, No. 4, p. 259-267.
Kato, Yukinari, et al; Molecular Identification of Aggrus/T1α as a Platelet Aggregation-inducing Factor Expressed in Colorectal Tumors, The Journal of Biological Chemistry, vol. 278, No. 51, Issue of Dec. 19, p. 51599-51605, 2003.
Kato, Yukinari, et al; "Aggrus: a diagnostic marker that distinguishes seminoma from embryonal carcinoma in testicular germ cell tumors", Oncogene (2004), 8552-8556.
Kunita, Akiko, et al; "The Platelet Aggregation-Inducing Factor Aggrus/Podoplanin Promotes Pulmonary Metastasis", Tumorigenesis and Neoplastic Progression, The American Journal of Pathology, vol. 170, No. 4, Apr. 2007.
Mishima, Kazuhiko, et al; "Increased expression of podoplanin in malignant astrocytic tumors as a novel molecular marker of malignant progression", Acta Neuropathol (2006) 111: 483-488.
Mishima, Kazuhiko, et al; Podoplanin expression in primary central nervous system germ cell tumors: a useful histological marker for the diagnosis of germinoma:, Acta Neuropathol (2006) 111: 563-568.
Fukunaga, M; "Expression of D2-40 in lymphatic endothelium of normal tissues and in vascular tumours"; Department of Pathology, the Jikei University School of Medicine, Tokyo, Japan; Histopatholoy 2005.
Kimura, Noriko, et al; "Podoplanin as a marker for mesothelioma", Department of Pathology and Laboratory Medicine, Tohoku Rosai Hospital et al., Pathology International 2005; 55: 83-86.
Wicki, Andreas, et al; "Tumor invasion in the absence of epithelial-mesenchymal transition: Podoplanin-mediated remodeling of the actin cytoskeleton", Institute of Biochemistry and Genetics, Department of Clinical-Biological Sciences, Center of Biomedicine, University of Basel, Switzerland, Cancer Cell vol . 9 p. 261 (2006).
Yuan, Ping, et al; "Overexpression of Podoplanin in Oral Cancer and Its Association with Poor Clinical Outcome", 2006 American Cancer Society.

(Continued)

*Primary Examiner* — Sheela J Huff
(74) *Attorney, Agent, or Firm* — Rankin, Hill & Clark LLP

(57) ABSTRACT

The present invention provides a monoclonal antibody or a functional fragment thereof, capable of recognizing Aggrus epitope that includes an amino-acid sequence represented by a sequence ID 1, 3, or 4, and the monoclonal antibody or the functional fragment thereof produced from a hybridoma with accession number of FERM BP-11446, FERM BP-11447, FERM BP-11448 or FERM BP-11449. The present invention provides the hybridoma, and further an Aggrus-CLEC-2 binding inhibitor and a pharmaceutical composition for inhibition of platelet aggregation, prevention of cancer metastasis, or treatment of tumor or cancer, including the monoclonal antibody or the functional fragment thereof.

14 Claims, 19 Drawing Sheets

(56) References Cited

OTHER PUBLICATIONS

Martin-Villar, Ester, et al; Characterization of human PA2.26 antigen (T1α-2, podoplanin), a small membrane mucin induced in oral squamous cell carcinomas:, Int. J. Cancer: 113, 899-910 (2005).

Kato, Yukinari, et al; Enhanced Expression of Aggrus (T1alpha/Podoplanin), a Platelet-Aggregation-Inducing Factor in Lung Squamous Cell Carcinoma:, Tumor Biology, 2005; 26: 195-200.
Nakazawa, et al. "Prevention of Hematogenous Metastasis by Neutralizing Mice and its Chimeric anti-Aggrus/Podoplanin Antibodies", Cancer Science, vol. 102, No. 11. Nov. 2011, 8 pages.
European Search Report dated Nov. 27, 2014, 8 pages.

\* cited by examiner

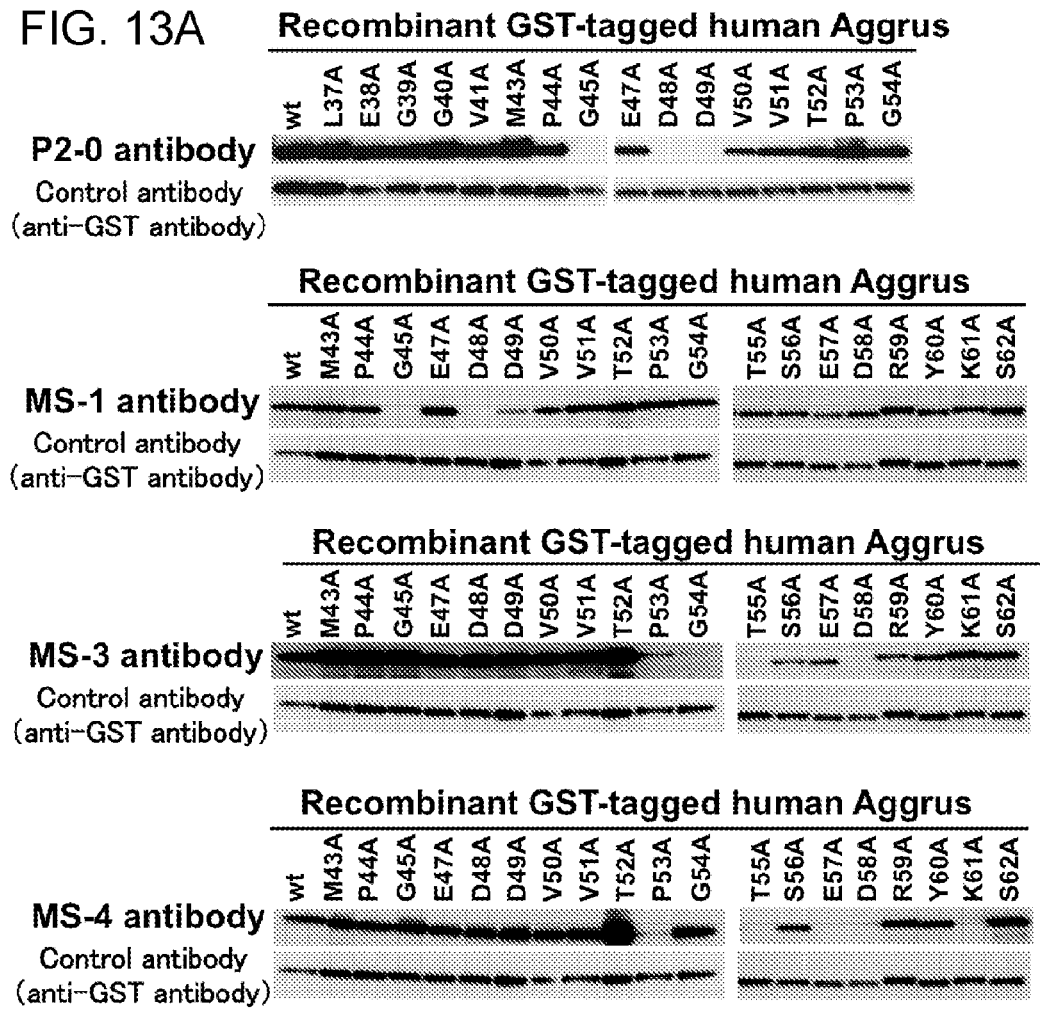

Reactivity against recombinant Fc-tagged Aggrus

Equilibrium dissociation constant ($K_D$) of P2-0 antibody
$9.3 \times 10^{-9}$ M Equilibrium dissociation constant ($K_D$) of MS-1 antibody
$9.0 \times 10^{-9}$ M Equilibrium dissociation constant ($K_D$) of MS-3 antibody
$6.3 \times 10^{-8}$ M Equilibrium dissociation constant ($K_D$) of MS-4 antibody
$2.0 \times 10^{-6}$ M

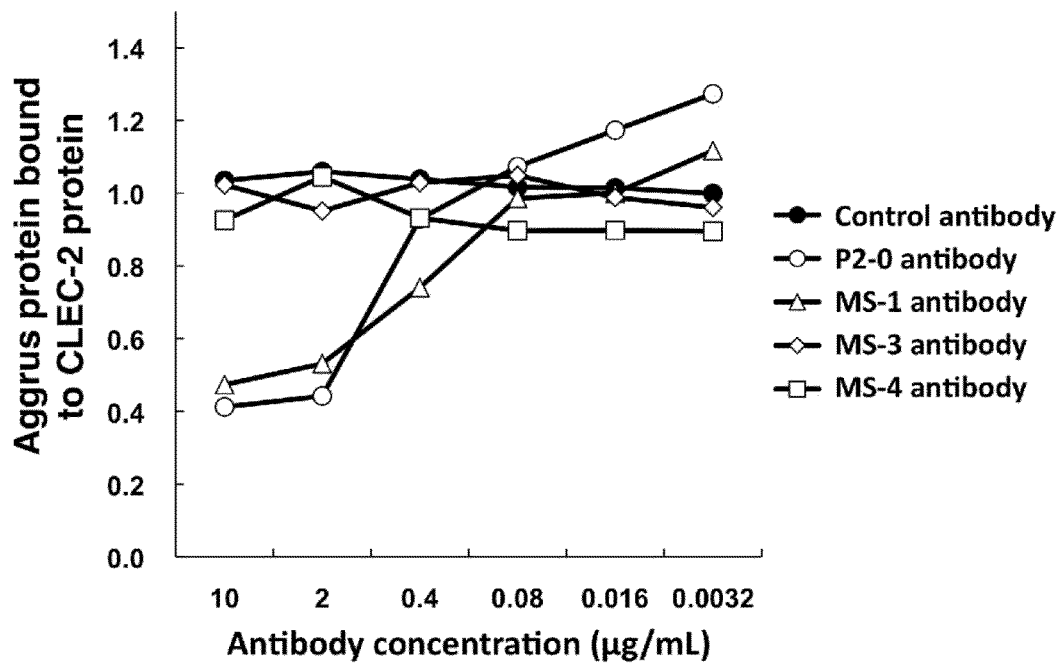
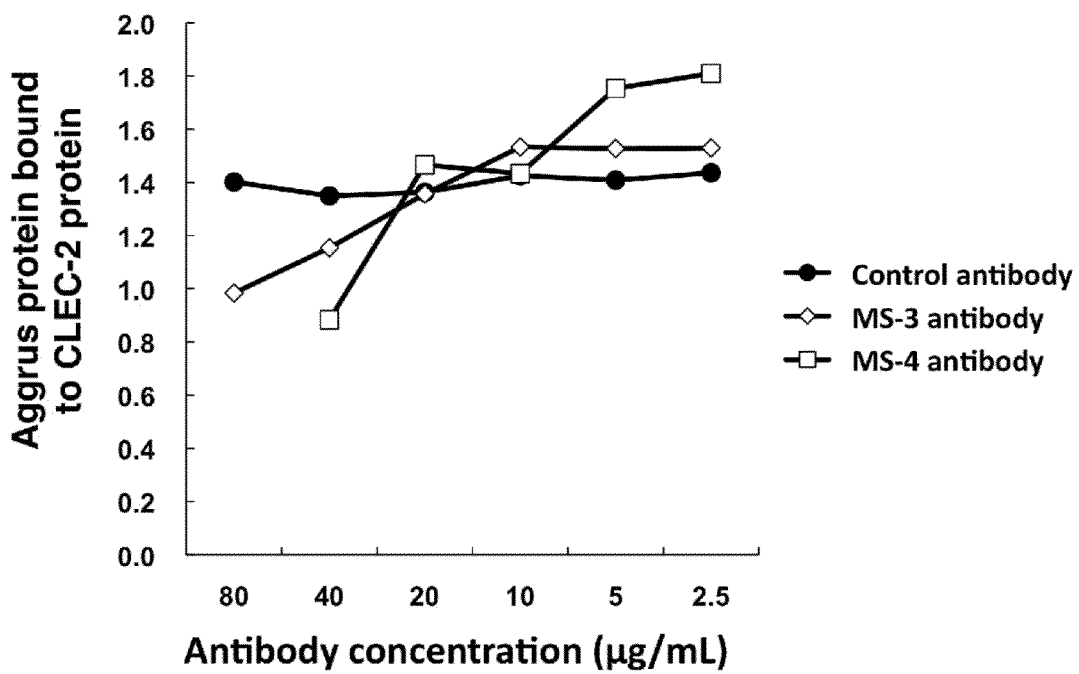

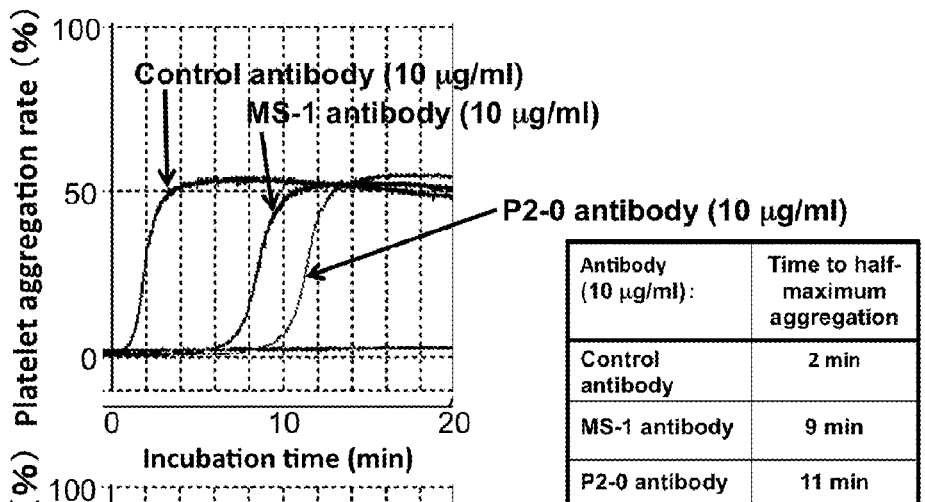
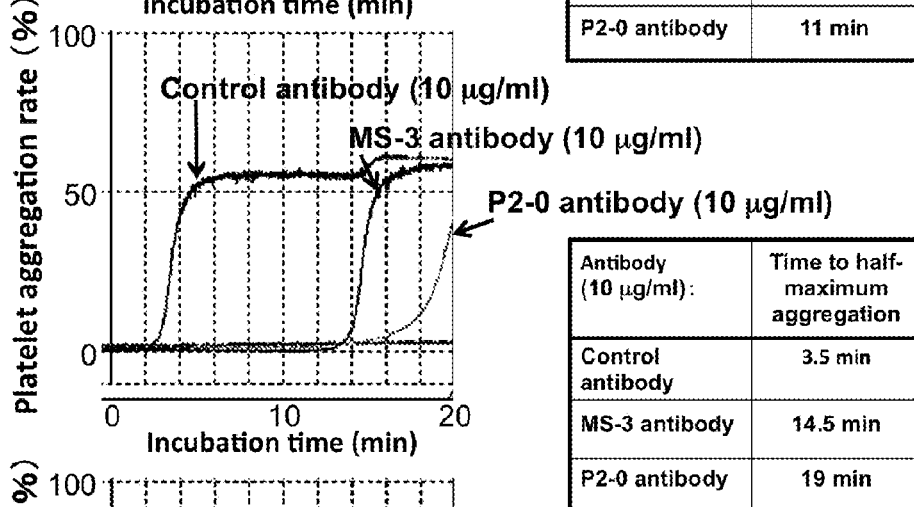
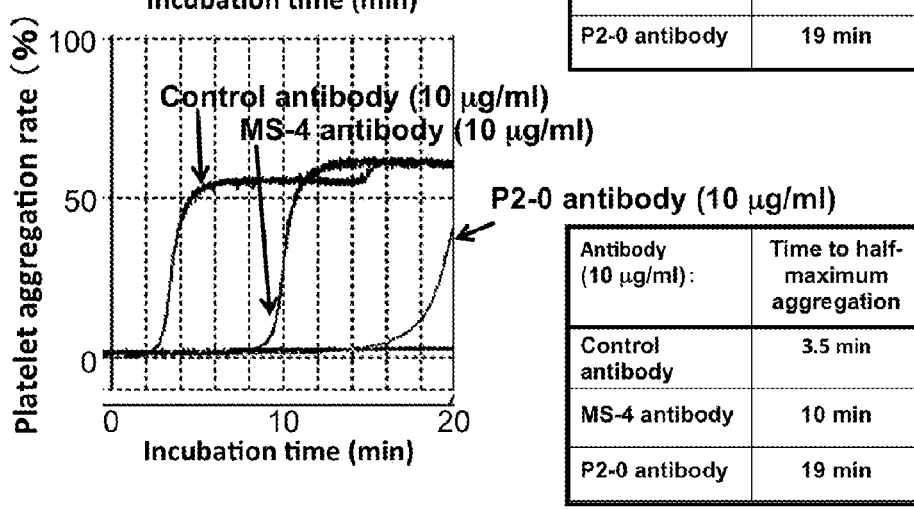

FIG.17A
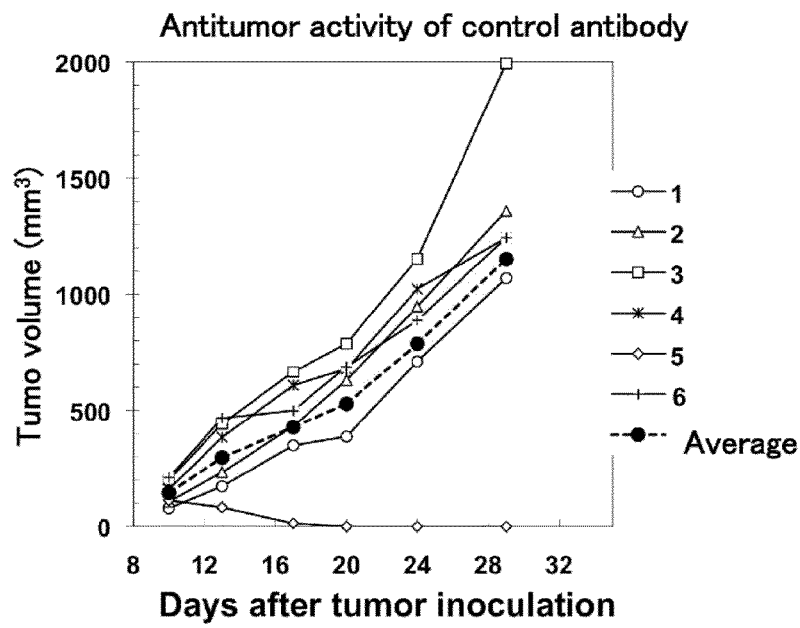
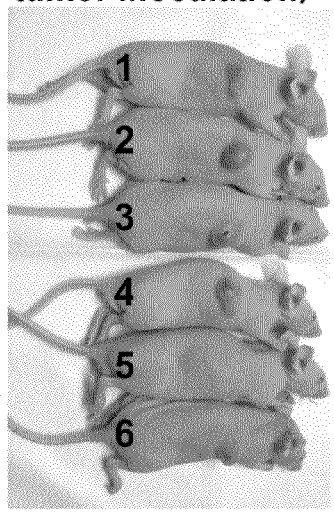
FIG.17B
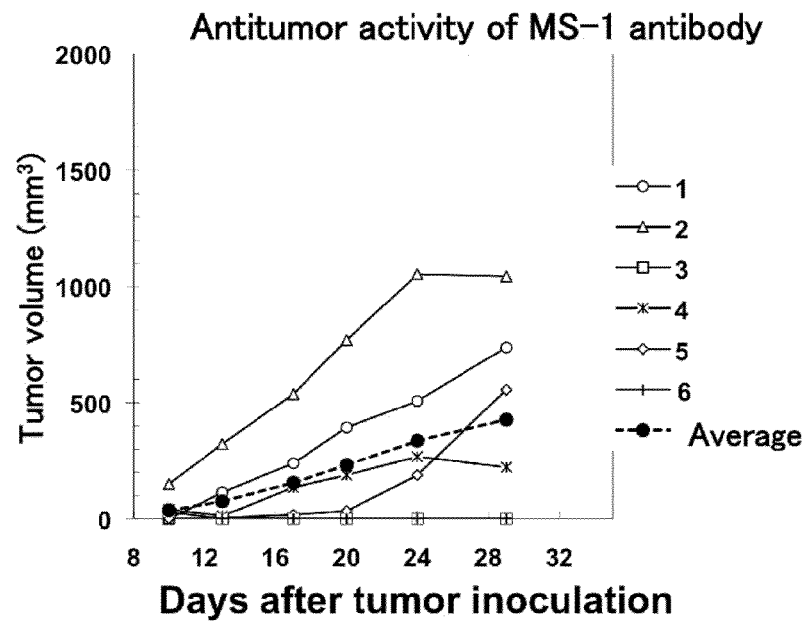
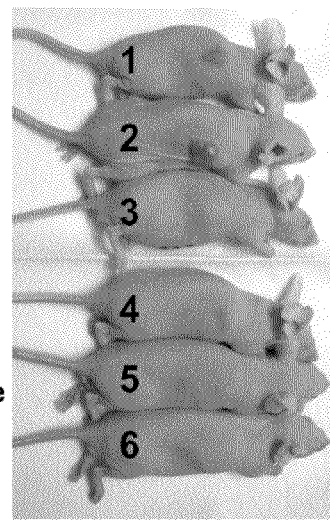

FIG.18A
MS-1 antibody suppressed spontaneous metastasis of Aggrus-transfected CHO cells
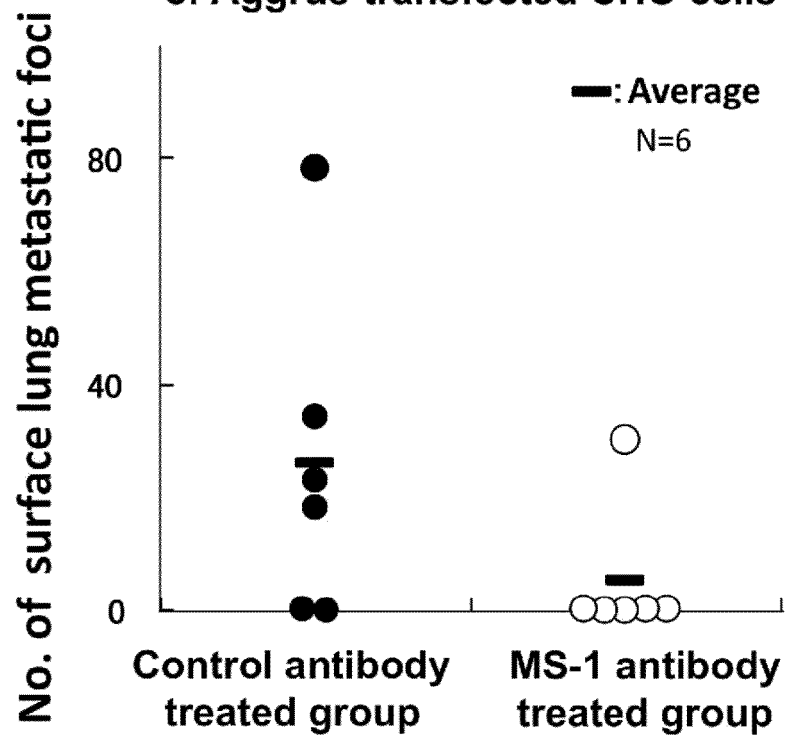
FIG.18B
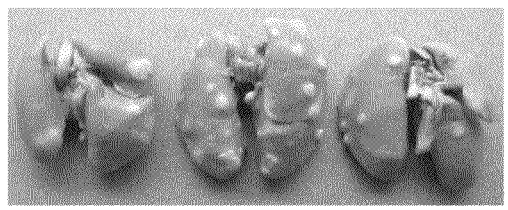
Control antibody treated mice (30 days after tumor inoculation)
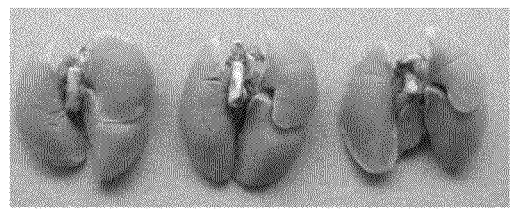
MS-1 antibody treated mice (30 days after tumor inoculation)

SEQUENCE LISTING

<160> NUMBER OF SEQ ID NOS: 15

<210> SEQ ID NO 1
<211> LENGTH: 9
<212> TYPE: PRT
<213> ORGANISM: Artificial Sequence
<220> FEATURE:
<223> OTHER INFORMATION: designed peptide

<400> SEQUENCE: 1

Pro Gly Ala Glu Asp Asp Val Val Thr
1               5

<210> SEQ ID NO 2
<211> LENGTH: 14
<212> TYPE: PRT
<213> ORGANISM: Artificial Sequence
<220> FEATURE:
<223> OTHER INFORMATION: designed peptide

```
<400> SEQUENCE: 2

Glu Gly Gly Val Ala Met Pro Gly Ala Glu Asp Val Val
1               5                   10

<210> SEQ ID NO 3
<211> LENGTH: 6
<212> TYPE: PRT
<213> ORGANISM: Artificial Sequence
<220> FEATURE:
<223> OTHER INFORMATION: desined peptide

<400> SEQUENCE: 3

Pro Gly Thr Ser Glu Asp
1               5

<210> SEQ ID NO 4
<211> LENGTH: 9
<212> TYPE: PRT
<213> ORGANISM: Artificial Sequence
<220> FEATURE:
<223> OTHER INFORMATION: designed peptide

<400> SEQUENCE: 4

Pro Gly Thr Ser Glu Asp Arg Tyr Lys
1               5

<210> SEQ ID NO 5
<211> LENGTH: 21
<212> TYPE: PRT
<213> ORGANISM: Artificial Sequence
<220> FEATURE:
<223> OTHER INFORMATION: designed peptide

<400> SEQUENCE: 5

Ala Met Pro Gly Ala Glu Asp Asp Val Val Thr Pro Gly Thr Ser Glu
1               5                   10                  15

Asp Arg Tyr Lys Ser
            20

<210> SEQ ID NO 6
<211> LENGTH: 25
<212> TYPE: PRT
<213> ORGANISM: Homo sapiens

<400> SEQUENCE: 6

Glu Thr Thr Gly Leu Glu Gly Gly Val Ala Met Pro Gly Ala Glu Asp
1               5                   10                  15

Asp Val Val Thr Pro Gly Thr Ser Glu
            20                  25

<210> SEQ ID NO 7
<211> LENGTH: 10
<212> TYPE: PRT
<213> ORGANISM: Artificial Sequence
<220> FEATURE:
<223> OTHER INFORMATION: designed peptide

<400> SEQUENCE: 7

Cys Thr Thr Gly Leu Glu Gly Gly Val Ala
1               5                   10

<210> SEQ ID NO 8
<211> LENGTH: 10
<212> TYPE: PRT
```

<213> ORGANISM: Artificial Sequence
<220> FEATURE:
<223> OTHER INFORMATION: designed peptide

<400> SEQUENCE: 8

Cys Gly Leu Glu Gly Gly Val Ala Met Pro
1               5                   10

<210> SEQ ID NO 9
<211> LENGTH: 10
<212> TYPE: PRT
<213> ORGANISM: Artificial Sequence
<220> FEATURE:
<223> OTHER INFORMATION: designed peptide

<400> SEQUENCE: 9

Cys Glu Gly Gly Val Ala Met Pro Gly Ala
1               5                   10

<210> SEQ ID NO 10
<211> LENGTH: 10
<212> TYPE: PRT
<213> ORGANISM: Artificial Sequence
<220> FEATURE:
<223> OTHER INFORMATION: designed peptide

<400> SEQUENCE: 10

Cys Gly Val Ala Met Pro Gly Ala Glu Asp
1               5                   10

<210> SEQ ID NO 11
<211> LENGTH: 10
<212> TYPE: PRT
<213> ORGANISM: Artificial Sequence
<220> FEATURE:
<223> OTHER INFORMATION: designed peptide

<400> SEQUENCE: 11

Cys Ala Met Pro Gly Ala Glu Asp Asp Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: designed peptide

<400> SEQUENCE: 12

Cys Pro Gly Ala Glu Asp Asp Val Val Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: designed peptide

<400> SEQUENCE: 13

Cys Ala Glu Asp Asp Val Val Thr Pro Gly
1               5                   10

<210> SEQ ID NO 14
<211> LENGTH: 10
<212> TYPE: PRT
<213> ORGANISM: Artificial Sequence

```
<220> FEATURE:
<223> OTHER INFORMATION: designed peptide

<400> SEQUENCE: 14

Cys Asp Asp Val Val Thr Pro Gly Thr Ser
1               5                   10

<210> SEQ ID NO 15
<211> LENGTH: 33
<212> TYPE: PRT
<213> ORGANISM: Homo sapiens

<400> SEQUENCE: 15

Thr Thr Gly Leu Glu Gly Gly Val Ala Met Pro Gly Ala Glu Asp Asp
1               5                   10                  15

Val Val Thr Pro Gly Thr Ser Glu Asp Arg Tyr Lys Ser Gly Leu Thr
            20                  25                  30

Thr
```

MOUSE ANTI-AGGRUS MONOCLONAL ANTIBODIES

FIELD OF THE INVENTION

The present invention relates to mouse anti-Aggrus monoclonal antibodies.

BACKGROUND

A platelet aggregation-inducing factor Aggrus (also known as podoplanin, gp44, etc.), a type-I transmembrane sialoglycoprotein, has been shown to be upregulated in many cancers such as different types of squamous cell carcinoma, mesothelioma, Kaposi's sarcoma, testicular germ cell tumors, and brain tumors (Non-patent documents 1-9). In some reports, Aggrus overexpression was correlated with a poorer prognosis, suggesting the important contribution of Aggrus to cancer progression (Non-patent documents 10, 11). Expression of Aggrus induced platelet aggregation, and promoted both experimental and spontaneous pulmonary metastasis in mice (Non-patent documents 11, 12). The platelet aggregation-inducing activity of Aggrus is directly linked to metastasis formation because the introduction of a point mutation that suppressed platelet aggregation attenuated the formation of pulmonary metastasis (Non-patent documents 11, 12). Cancer cell-induced platelet aggregation is believed to form a large cancer cell-platelet aggregate, resulting in enhanced cancer cell embolization in the microvasculature and protection from immunological assault in the circulation. The C-type lectin-like receptor 2 (CLEC-2) expressed on platelets was recently identified as one of the counter-receptors of Aggrus. When CLEC-2 binds to Aggrus expressed on tumor cells, it generates activation signals in platelets with no requirement for plasma components. Aggrus's critical domains for the interaction to CLEC-2 have been identified (Non-patent document 13).

A monoclonal antibody (mAb) can bind firmly and specifically to cell surface antigens and can induce an immunological response in the target cell. Thus, many mAbs are now used in cancer therapy. The mAbs used in cancer therapy show anti-cancer effects via three representative modes of action: neutralizing, antibody-dependent cellular cytotoxic (ADCC), and complement-dependent cytotoxic (CDC) activities. The mAbs, including bevacizumab and cetuximab, could neutralize activation of signal pathways by inhibiting either ligand-receptor binding or receptor oligomerization. Because cancer proliferation depends on activation of signal pathways, neutralization of signal pathway induces tumor cell death. Moreover, the mAbs, including rituximab and trastuzumab, could also induce immune response to target cancer cells via their fragment crystallizable (Fc) region. Complements and effector cells such as macrophage, natural killer (NK), and neutrophil can kill target cancer cells by recognizing Fc region of mAbs that bind cancer specific antigens. These three modes of action are specified by the isotype and subclass of the antibody, the traits of the antigen, and the recognition site.

Many mAbs against Aggrus have been established so far, but most of them cannot interfere with Aggrus-CLEC-2 interaction. Although one rat mAb, designated as NZ-1, is known as the Aggrus mAb capable of inhibiting Aggrus-CLEC-2 interaction and platelet aggregation (Non-patent document 14), however it is a rat antibody and cannot be precisely examined in universally-used mouse cancer model because of the species barrier.

PRIOR ART DOCUMENT

Non-Patent Document

[Non-patent document 1] Kato Y, Kaneko M, Sata M, Fujita N, Tsuruo T, Osawa M. Enhanced expression of Aggrus (T1α/podoplanin), a platelet-aggregation-inducing factor in lung squamous cell carcinoma. Tumor Biol 2005; 26: 195-200.

[Non-patent document 2] Martin-Villar E, Scholl F G, Gamallo C et al. Characterization of human PA2.26 antigen (T1α-2, podoplanin), a small membrane mucin induced in oral squamous cell carcinomas. Int J Cancer 2005; 113: 899-910.

[Non-patent document 3] Yuan P, Tenam S, EI-Naggar A et al. Overexpression of podoplanin in oral cancer and its association with poor clinical outcome. Cancer 2006; 107: 563-569.

[Non-patent document 4] Wicki A. Lehembre F, Wick N, Hantusch B, Kerjaschki D, Christofori G. Tumor invasion in the absence of epithelial-mesenchymal transition: podoplanin-mediated remodeling of the actin cytoskeleton. Cancer Cell 2006; 9: 261-272.

[Non-patent document 5] Kimura N, Kimura I. Podoplanin as a marker for mesothelioma. Pathol Int 2005; 55: 83-86.

[Non-patent document 6] Fukunaga M. Expression of D2-40 in lymphatic endothelium of normal tissues and in vascular tumours. Histopathology 2005; 46: 396-402.

[Non-patent document 7] Kato Y, Sasagawa I, Kaneko M, Osawa M, Fujita N, Tsuruo T. Aggrus: a diagnostic marker that distinguishes seminoma from embryonal carcinoma in testicular germ cell tumors. Oncogene 2004; 23: 8552-8556.

[Non-patent document 8] Mishima K, Kato Y, Kaneko M K et al. Podoplanin expression in primary central nervous system germ cell tumors: a useful histological marker for the diagnosis of germinoma. Acta Neuropathol 2006; 111: 563-568.

[Non-patent document 9] Mishima K, Kato Y, Kaneko M K, Nishikawa R, Hirose T, Matsutani M. Increased expression of podoplanin in malignant astrocytic tumors as a novel molecular marker of malignant progression. Acta Neuropathol 2006; 111: 483-488.

[Non-patent document 10] Yuan P, Temam S, El-Naggar A, Zhou X, Liu D D, Lee J J, Mao L. Overexpression of podoplanin in oral cancer and its association with poor clinical outcome. Cancer 2006; 107: 563-569.

[Non-patent document 11] Kunita A, Kashima T G, Morishita Y, Fukayama M, Kato Y, Tsuruo T, Fujita N. The platelet aggregation-inducing factor aggrus/podoplanin promotes pulmonary metastasis. Am J Pathol 2007; 170: 1337-1347.

[Non-patent document 12] Kato Y, Fujita N, Kunita A, Sato S, Kaneko M, Osawa M, Tsuruo T. Molecular identification of Aggrus/T1alpha as a platelet aggregation-inducing factor expressed in colorectal tumors. J Biol Chem. 2003; 278: 51599-51605.

[Non-patent document 13] Kato Y, Kaneko M K, Kunita A et al. Molecular analysis of the pathophysiological binding of the platelet aggregation-inducing factor podoplanin to the C-type lectin-like receptor CLEC-2. Cancer Sci 2008; 99: 54-61.

[Non-patent document 14] Kato Y, Kaneko M K, Kuno A et al. Inhibition of tumor cell-induced platelet aggregation using a novel anti-podoplanin antibody reacting with its plateletaggregation-stimulating domain. Biochem Biophys Res Commun 2006; 349: 1301-1307.

DISCLOSURE OF INVENTION

Problem to be Solved by the Invention

The present invention has been made in order to provide effective components of pharmaceutical compositions targeting Aggrus for cancer or thrombosis therapy.

Means for Solving the Problem

As a result of earnest studies, the inventors of the present invention established hybridomas that produce mAbs inhibiting Aggrus-CLEC-2 interaction and platelet aggregation. The inventors found that mAbs produced by these hybridomas recognize Aggrus epitopes of an amino-acid sequence shown in Sequence ID 1 (Pro Gly Ala Asp Asp Val Val Thr), Sequence ID 3 (Pro Gly Thr Ser Glu Asp), or Sequence ID 4 (Pro Gly Thr Ser Glu Asp Arg Tyr Lys), that mAbs inhibit the Aggrus-CLEC-2 interaction in a concentration-dependent manner, and that mAbs exhibit platelet-aggregation neutralizing ability and pulmonary metastasis inhibitory ability.

Therefore, the present invention provides mouse mAbs and function fragments thereof (1) which recognize Aggrus epitopes represented by Sequence ID 1, 3, or 4.

Moreover, the present invention provides the mAbs according to (1) or the functional fragments thereof (2) produced by hybridomas deposited as FERM BP-11446, FERM BP-11447, FERM BP-11448, or FERM BP-11449.

Furthermore, the present invention provides humanized or murine/human chimeric mAbs or their functional fragments (3) according to (1) or (2).

The present invention provides hybridomas of deposit ID of FERM BP-11446, FERM BP-11447, FERM BP-11448, or FERM BP-11449 (4).

The present invention provides Aggrus-CLEC-2 interaction inhibitors (5) including mAbs or the functional fragment thereof according to (1)-(3).

The present invention provides pharmaceutical compositions (6) containing mAbs or the functional fragments thereof described in (1)-(3) for inhibition of platelet-aggregation, inhibition of cancer metastasis, or treatment of tumor or thrombosis.

Moreover, the present invention provides the pharmaceutical compositions (7) according to (6) wherein thrombosis is cerebral infarction or myocardial infarction.

Furthermore, the present invention provides the pharmaceutical compositions (8) according to (6), wherein cancer or tumor is squamous cell carcinoma, fibrosarcoma, mesothelioma, Kaposi's sarcoma, testicular germ cell tumor, brain tumor, or bladder cancer.

Desirably the present invention provides the pharmaceutical compositions (9) according to (8), wherein cancer or tumor is squamous cell carcinoma, mesothelioma, testicular germ cell tumor, or bladder cancer.

Effects of Invention

The mouse mAbs, designated as P2-0, MS-1, MS-3, or MS-4, produced by hybridomas that the present inventors established recognizes Aggrus epitopes of the amino-acid sequence shown in Sequence ID 1, 3, or 4 when analyzed in vivo and in vitro, and inhibits Aggrus-CLEC-2 binding in a concentration dependent manner. Moreover, the mAbs according to the present invention exhibited platelet-aggregation inhibitory activity and pulmonary metastasis inhibitory activity. The humanized antibodies (murine/human chimeric antibodies) according to the present invention exhibited cancer metastasis inhibitory activity against lower Aggrus expressing cancer cells. The mAbs according to the present invention exhibited different reactivity from a known rat mAb against native Aggrus protein, and unexpectedly inhibited Aggrus-dependent pulmonary metastasis by lower concentration than the known rat mAb. Because each mAb of the present invention recognizes different epitope, using these antibodies have a high advantage to overcome the drug resistant mutation that is frequently occurred in cancer by using another antibody. Moreover, it is not necessary to consider the specie's barrier during development as antitumor drugs using mice models in which human cancer is implanted (mice xenograft models) because the mAbs of the present invention are mouse mAbs. Though rat/mouse-chimeric antibody is able to be generated by cloning and ligating the complementarity determining regions (CDR) of rat antibody to mouse Fc region, transfection of chimeric antibody-expressing vector to antibody producing cells, such as CHO cells, and large culture of the transfectants is necessary for the preparation of large amount of chimeric antibody. Compared with the case of preparation of mouse antibody from mouse ascites, the method to culture the transfectants in a selection medium is high cost and may not suitable for practical use. Therefore, mAbs established by the present invention have especial benefits, for example, in generating pharmaceutical compositions for human cancer using mouse xenograft models.

BRIEF DESCRIPTION OF THE DRAWINGS

FIG. 1 is the schematic representation showing refinement of recognized epitope using synthetic peptides of P2-0 mAb.

FIG. 2 shows that P2-0 mAb inhibits Aggrus-CLEC-2 interaction in a concentration dependent manner.

FIG. 3 shows that P2-0 mAb exhibits platelet-aggregation inhibitory activity.

FIG. 4 shows that P2-0 mAb exhibits cancer metastasis inhibitory activity.

FIG. 5 shows that humanized P2-0 mAb (murine/human chimeric P2-0 mAb) exhibits platelet aggregation inhibitory activity.

FIG. 6 shows that humanized P2-0 mAb (murine/human chimeric P2-0 mAb) exhibits cancer metastasis inhibitory activity.

FIG. 7 shows that humanized P2-0 mAb (murine/human chimeric P2-0 mAb) also exhibits antimetastatic activity against low Aggrus-expressing cells (HT1080).

FIG. 8 shows that P2-0 mAb recognizes endogenous Aggrus protein expressed in human bladder cancer cell lines.

FIG. 9 shows the difference in recognition ability between NZ-1 mAb and P2-0 mAb in Western blotting analysis.

FIG. 10A shows a result of analysis of NZ-1 mAb in FACS analysis indicating a difference in Aggrus recognition ability between NZ-1 mAb (FIG. 10A) and P2-0 mAb (FIG. 10B).

FIG. 10B shows a result of analysis of P2-0 mAb in FACS analysis indicating a difference in Aggrus recognition ability between NZ-1 mAb (FIG. 10A) and P2-0 mAb (FIG. 10B).

FIG. 11 shows the difference in pulmonary metastasis inhibitory activities between NZ-1 mAb and P2-0 mAb.

FIG. 12 shows that MS-1 (FIG. 12A), MS-3 (FIG. 12C), and MS-4 (FIG. 12C) mAbs recognize human Aggrus on CHO cells introduced with human Aggrus genes by a flow cytometry analysis.

[FIG. 13A-13B] FIG. 13 shows a refinement of recognition epitope of MS-1, MS-3, or MS-4 mAb using Aggrus proteins harboring Ala mutations.

FIG. 14 shows binding between a recombinant human Aggrus protein and P2-0 (FIG. 14A), MS-1 (FIG. 14B), MS-3 (FIG. 14C), or MS-4 (FIG. 14D) using surface plasmon resonance.

[FIG. 15A-15B] FIG. 15 shows that P2-0, MS-1, MS-3, or MS-4 mAb inhibits Aggrus-CLEC-2 interaction.

[FIG. 16A-16C] FIG. 16 shows that P2-0, MS-1, MS-3, or MS-4 mAb possesses platelet-aggregation inhibitory activity.

[FIG. 17A-17B] FIG. 17 shows that MS-1 mAb exhibits antitumor activity against Aggrus-expressing cells.

[FIG. 18A-18B] FIG. 18 shows that MS-1 mAb inhibits spontaneously lung metastasis of human Aggrus-expressing cells.

FIG. 19 shows that MS-1 and MS-3 mAbs possess pulmonary metastasis inhibitory activity.

DETAILED DESCRIPTION OF PREFERRED EMBODIMENTS

Figure 1A:
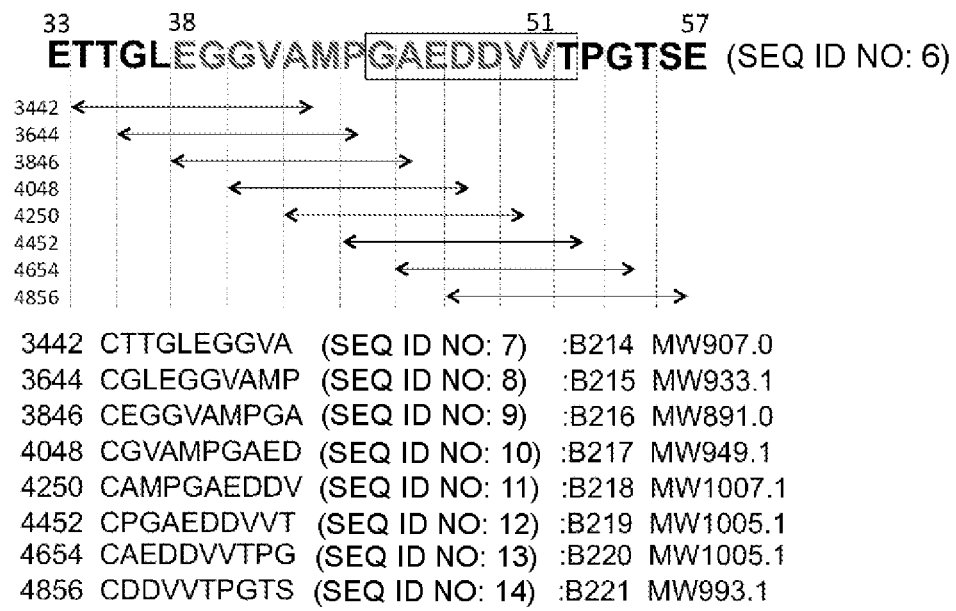
[FIG. 1A-1b]

Aggrus is also known as gp44, podoplanin and the like.

An "anti-Aggrus monoclonal antibody" refers to a monoclonal antibody or derivative which specifically binds to Aggrus, and includes fragments of the antibody (in the present specification, referred to as "functional fragment") showing virtually the same antigen specificity as the original antibody. The functional fragment of antibody includes the functional fragments of antibodies such as Fab, Fab', F(ab')$_2$, a single-chain antibody (scFv), disulfide stabilized V region fragment (dsFv), or peptide including CDR. The antibody in the present invention may be prepared by conventional method, including immunizing animal, preferably mice, and collecting spleen cells for preparing hybridoma by fusing with appropriate cells, as will be explained later.

As a suitable example of the mouse monoclonal antibody to Aggrus, the monoclonal antibody produced from hybridoma deposited on Feb. 18, 2011 with International Patent Organism Depositary, National Institute of Advances Industrial Science and Technology, AIST Tsukuba Center No. 6, 1-1, Higashi 1-chrome, Tsukuba-shi, Ibaraki-ken 305-8566 Japan (IPDC-AIST) in accordance with the Budapest Treaty on the Deposit of Microorganisms, and accorded Accession No. FERM BP-11446 and hybridomas deposited on Dec. 28,2011 with IPDC-AIST in accordance with the Budapest Treaty on the Deposit of Microorganisms, and accorded Accession Nos. FERM BP-11447, FERM BP-11448 and FERM BP-11449,may be given. Further, other antibodies having similar binding characteristics are preferable as the anti-Aggrus monoclonal antibody of the present invention.

A humanized antibody in which antibodies of animals other than human is made into a human chimeric antibody or a human CDR transplanted antibody using gene recombination technology may be favorably used in the present invention. The human chimeric antibody is an antibody in which a variable region of the antibody (hereinafter referred to as V region) is an antibody of an animal other than human, and a constant region (hereinafter referred to as C region) is an antibody of a human (Morrioson S. L. et al., Proc Natl Acad Sci USA. 81 (21), 6851-6855, 1984), and the human CDR transplanted antibody is an antibody in which an amino-acid sequence of the CDR in the V region of the antibody of animal other than human is transplanted to an appropriate position of a human antibody (Jones P. T. et al., Nature, 321 (6069), 522-525, 1986). The humanized antibody has smaller side effects than the antibodies of animals other than human, when administered to human, and a treatment effect thereof continues for a long time. Further, the humanized antibody may be produced as molecules of various manner using the gene recombination technology.

The present invention provides, as another embodiment, an Aggrus-CLEC-2 binding inhibitor and a pharmaceutical composition for inhibition of platelet aggregation, prevention of cancer metastasis, or treatment of tumor or cancer, comprising the monoclonal antibody or the fragment comprising functional fragment thereof. The thrombosis is preferably cerebral infarction or myocardial infarction. The cancer or tumor is preferably squamous cell carcinoma, fibrosarcoma, mesothelioma, Kaposi's sarcoma, testicular germ cell tumor, brain tumor, or bladder cancer. In the specification of the present invention, the term "cancer" and "tumor" are used as a term having the same meaning.

As types of form of the pharmaceutical composition, for example, oral preparations such as pills, powder, balls, powder medicines, fine grain agents, hard or soft capsules, film coatings, pellets, sublingual formulations, and pastes, parenteral agents such as injectable drugs, suppositories, transdermal drugs, ointments, empastrums, and liquids for external use, may be given, and the person skilled in the art may select the most suitable form according to an administration route or an administration target and the like. The anti-Aggrus monoclonal antibody as an active ingredient may be contained from 0.1 to 99.9 percent by weight in the formulation.

The administration amount of the active ingredient may differ from the administration target, a target organ, a symptom, an administration method and the like, but in a case of an oral administration, generally, to a patient (60 kg) per day, it is approximately 0.1 μg to 1000 mg, preferably approximately 1.0 μg to 100 mg, and more preferably approximately 1.0 mg to 50 mg. In a case of a parenteral administration, a single administration amount may differ from the administration target, the target organ, the symptom, the administration method and the like, but it is preferable to administer, per day, approximately 0.01 to 30 mg, preferably approximately 0.1 to 20 mg, and more preferably approximately 0.1 to 10 mg by an intravenous injection. However, the amount may finally be determined arbitrarily, by the determination of a doctor or a veterinarian, taking into consideration the type of form, the administration method, age and weight of patient, the symptom of patient and the like.

Hereinafter, the present invention will be explained in detail with Embodiments.

Embodiment 1

Immunogen to Establish Hybridomas which Produce Mouse Anti-Human Aggrus mAbs

A human aggrus cDNA region encoding the TT679 antigen (14 a.a. located on 38-51 of Aggrus protein, Sequence ID 2: Glu Gly Gly Val Ala Met Pro Gly Ala Glu Asp Asp Val Val) was cloned and connected eight times repeatedly (TT679-repeat) on a pGEX-6P-3 vector (GE Healthcare, Buckinghamshire, UK). BL21 *Escherichia Coli* (Invitrogen, Carlsbad, Calif.) was transformed with these vectors, and GST-tagged recombinant proteins were purified using Glutathione Sepharose (GE Healthcare).

Sensitization

Six-week-old female BALB/c mice (bought from Charles-river Laboratories Japan, Inc., bred according to common procedure) were immunized by neck subcutaneous injections of the immunogen obtained in above with Freund's complete adjuvant (Difco Laboratories, Detroit, Mich.). Every other week, intraperitoneal immunization was performed.

Establishment of Hybridomas

Spleen cells harvested according to common procedure were fused with mouse myeloma P3U1 cells using polyethylene glycol 4000 (Merck, NJ). Hybridoma cells were cultured and selected in RPMI1640 (Sigma) containing hypoxanthine, aminopterin, and thymidine. As a result, 15 clonal hybridomas were established.

Embodiment 2

Analysis of Mouse Anti-Human Aggrus mAbs Verification by Western Blotting

Among anti-Aggrus mAb-producing hybridomas, one hybridoma which produces P2-0 mAb was deposited to National Institute of Technology and Evaluation-International Patent Organism Depositary on Feb. 18, 2011, and was assigned deposit ID of FERM BP-11446 (identical to deposit ID FERM P-22069). P2-0 mAb was confirmed to recognize human Aggrus by flow cytometry analysis and western blotting. Moreover, when western blotting was performed using prepared Aggrus mutants with deficient amino acid Sequence ID 2, P2-0 mAb could not recognize the same.

Embodiment 3

Exploring of Epitope

Figure 1B:
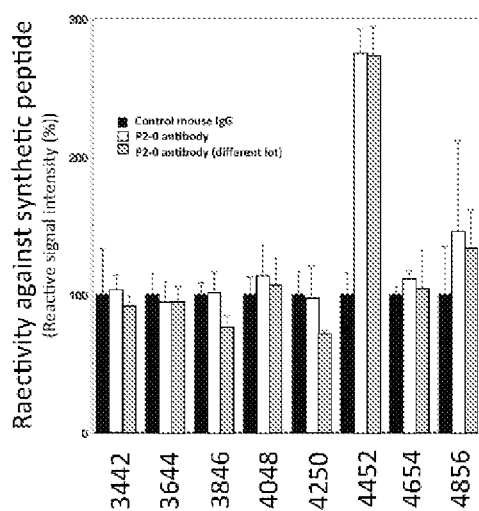

As shown in FIG. 1, reactivity of P2-0 mAb to various peptides for chemical synthesis was examined by ELISA method. As a result, P2-0 mAb exhibited high reactivity to one peptide containing 44-52 amino acids sequence (Sequence ID 1).

Embodiment 4

Inhibition Assay of Aggrus-CLEC-2 Interaction

Figure 2:
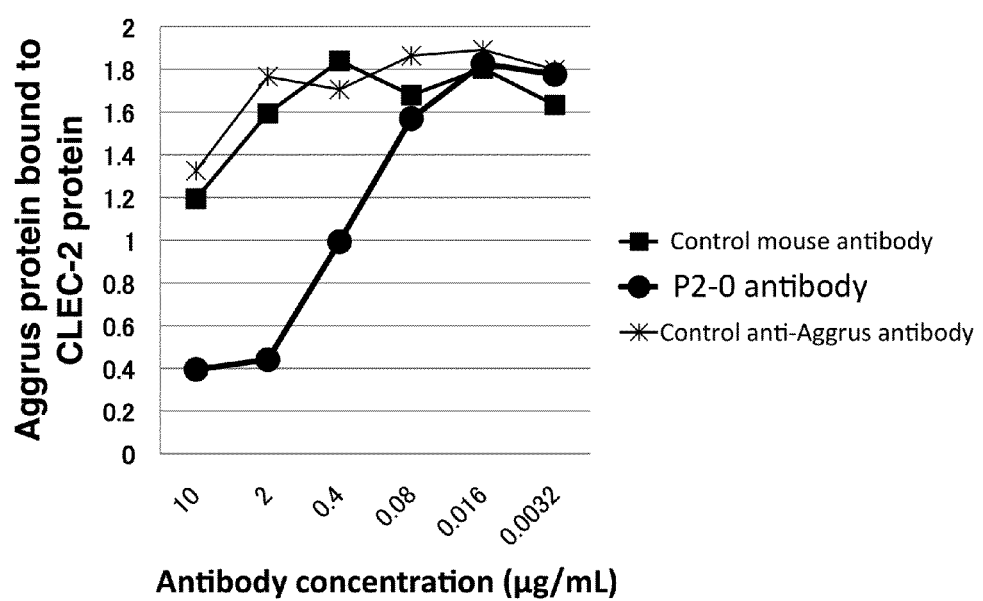
[FIG. 2]

By using recombinant Aggrus and CLEC-2 proteins prepared from mammalian cells, Aggrus-CLEC-2 interaction was detected by ELISA method. Effects of Aggrus-CLEC-2 interaction were examined under presence of Aggrus mAbs. As shown in FIG. 2, P2-0 mAb inhibited Aggrus-CLEC-2 interaction in a concentration dependent manner.

Embodiment 5

Inhibition Assay of Platelet Aggregation

Figure 3:
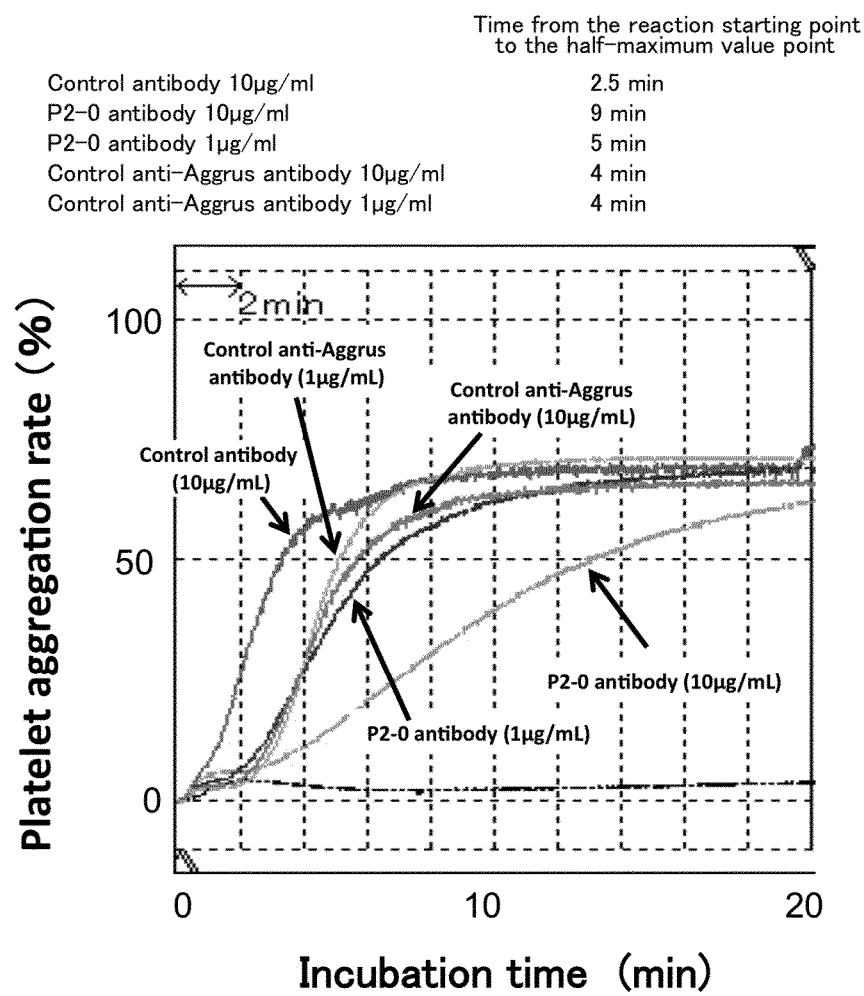
[FIG. 3]

Although parental CHO and CHO/mock cells were known to be incapable of inducing platelet aggregation, Aggrus overexpressing CHO (CHO/Aggrus) cells induced platelet aggregation. In an in vitro platelet aggregation analysis by monitoring of light transmittance, the time from reaction-starting point until reaching a half of maximum value point was compared. As shown in FIG. 3, Aggrus-induced platelet aggregation was attenuated by P2-0 antibody addition in a concentration-dependent manner.

Embodiment 6

Inhibition Assay of Pulmonary Metastasis

Figure 4:
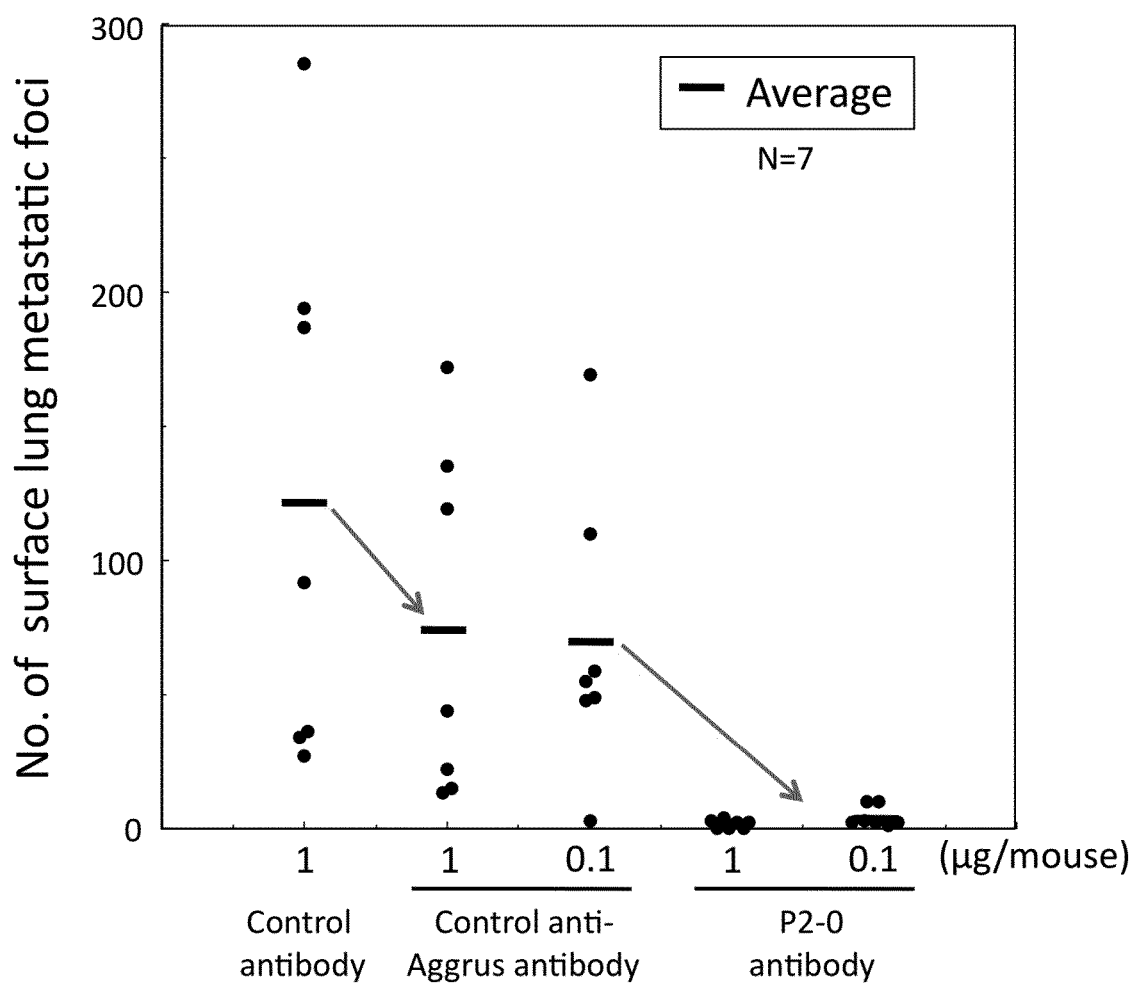
[FIG. 4]

The effects of mAbs on experimental pulmonary metastasis in vivo of intravenously injected CHO cells introduced with human Aggrus gene were examined. It is known that CHO cells show metastatic ability from forced expression of Aggrus. As shown in FIG. 4, P2-0 mAb showed extremely high pulmonary metastasis inhibitory activity by concurrent administration of extremely small amount such as 0.1 μg/mouse, indicating that P2-0 mAb possessed Aggrus dependent hematogenously metastasis inhibitory activity as well as Aggrus neutralizing ability.

Embodiment 7

Generation and Verification of Humanized (Murine/Human Chimeric) Antibody

Figure 5:
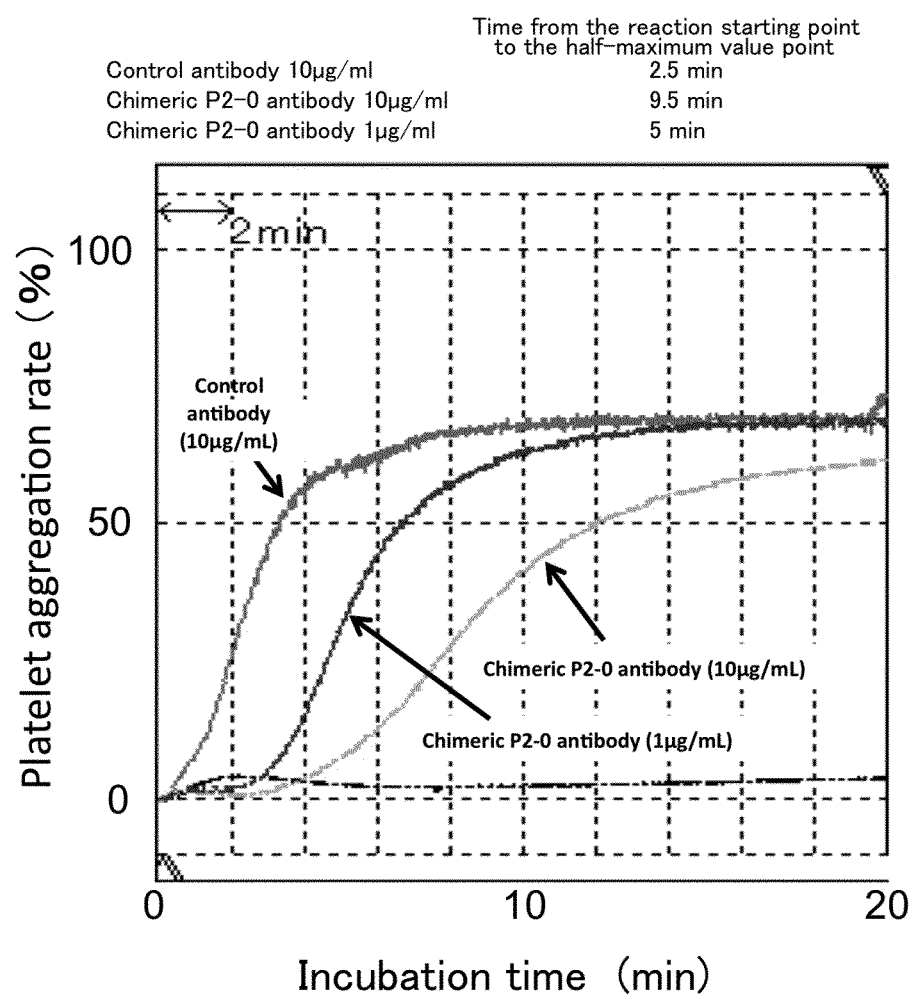
[FIG. 5]
Figure 6:
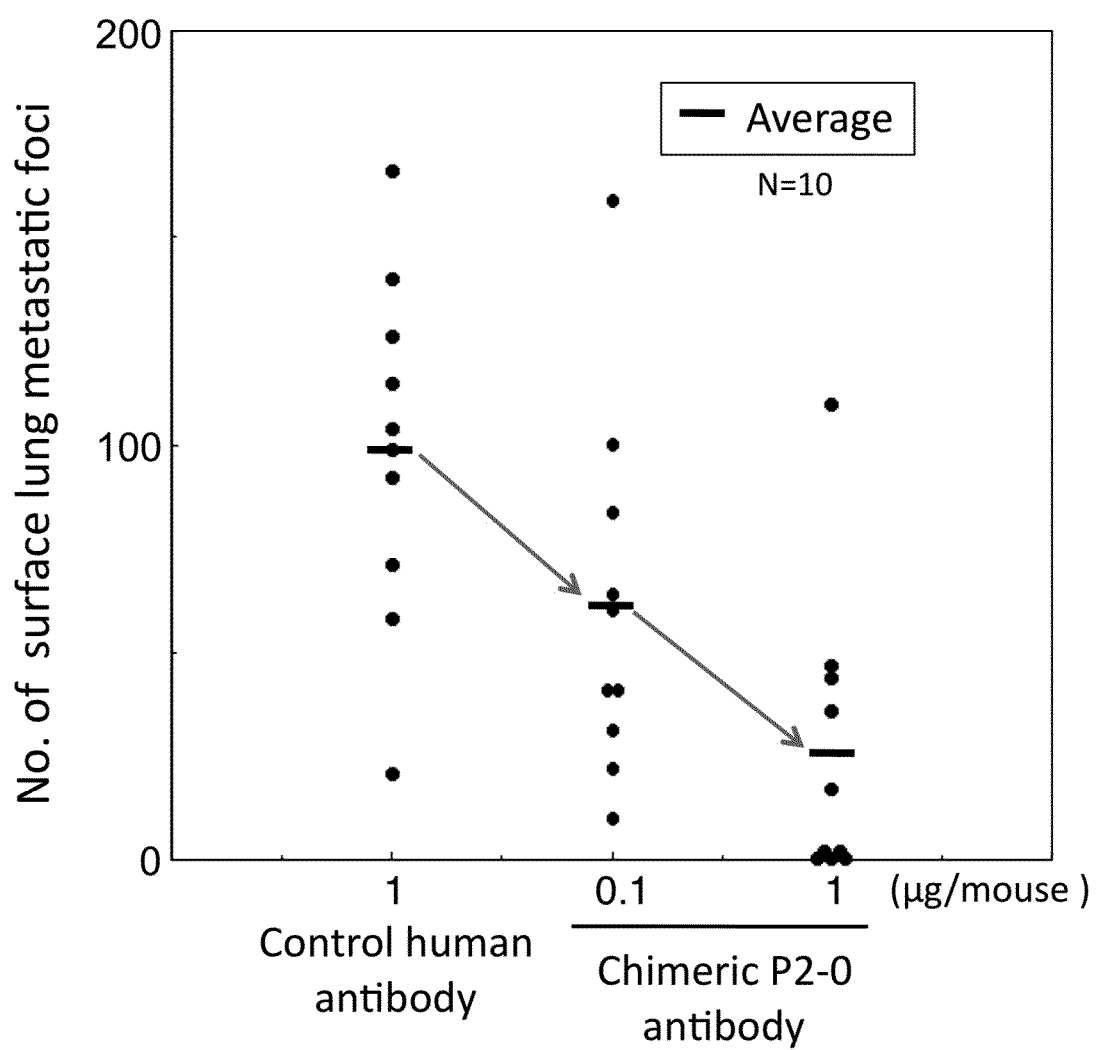
[FIG. 6]
Figure 7:
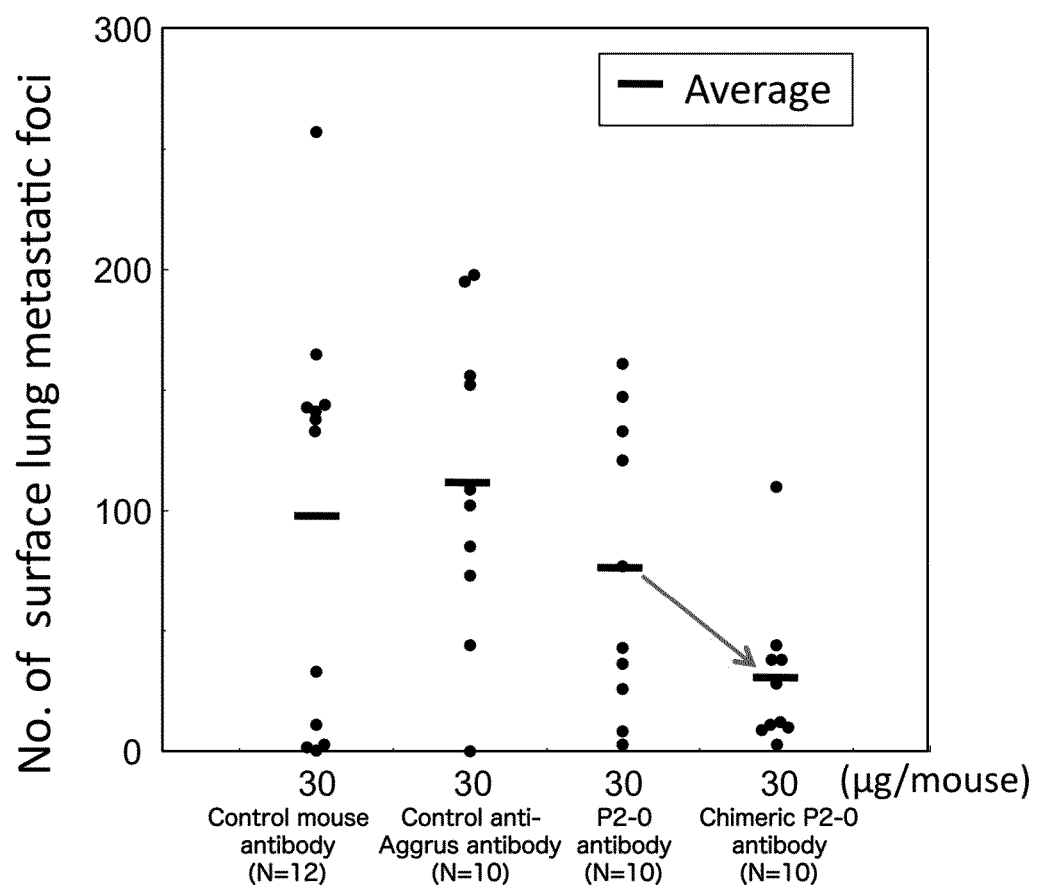
[FIG. 7]

In order to put to practical use, humanized P2-0 antibody (murine/human chimeric P2-0 antibody) was generated by cloning variable region of P2-0 and by ligating the same according to common procedure into the constant region of human IgG1. The humanized P2-0 antibody (murine/human chimeric P2-0 antibody) was confirmed to recognize simian Aggrus. Similar to original P2-0 antibody, humanized P2-0 antibody (murine/human chimeric P2-0 antibody) showed inhibition of platelet aggregation (FIG. 5) and metastasis inhibitory activity (FIG. 6). As shown in FIG. 7, humanized P2-0 antibody (murine/human chimeric P2-0 antibody) also showed metastasis inhibitory activity of low Aggrus expressing cells (HT1080 cells).

Embodiment 8

Screening of Aggrus-Expressing Cancer and Comparison of Rat Anti-Aggrus mAb (NZ-1 Antibody)

By real-time PCR method using cDNA templates (TissueScan cDNA Panel commercially available from OriGene) that were prepared from clinical samples of bladder cancer, frequently upregulation of Aggrus expression was identified in bladder cancer.

Figure 8:
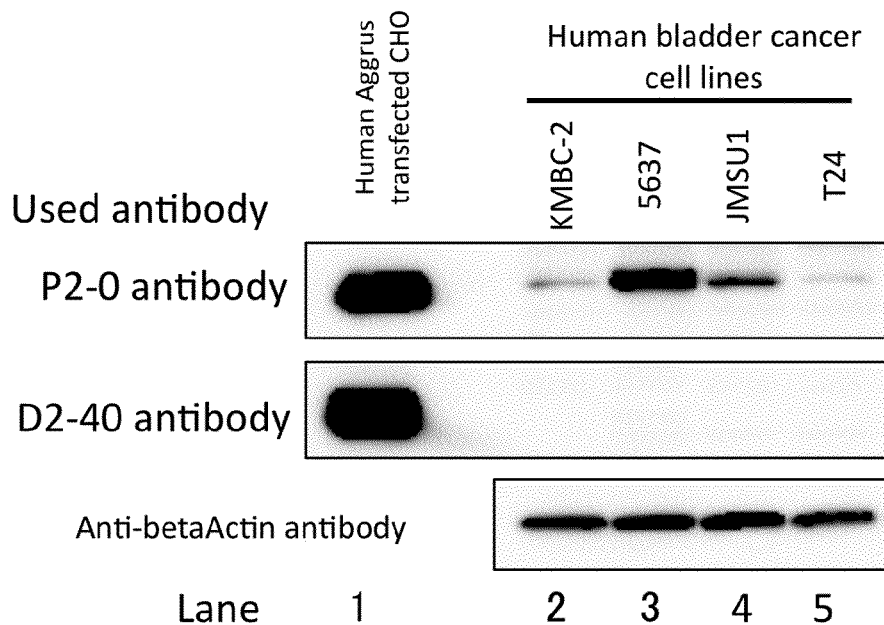
[FIG. 8]
Figure 9:
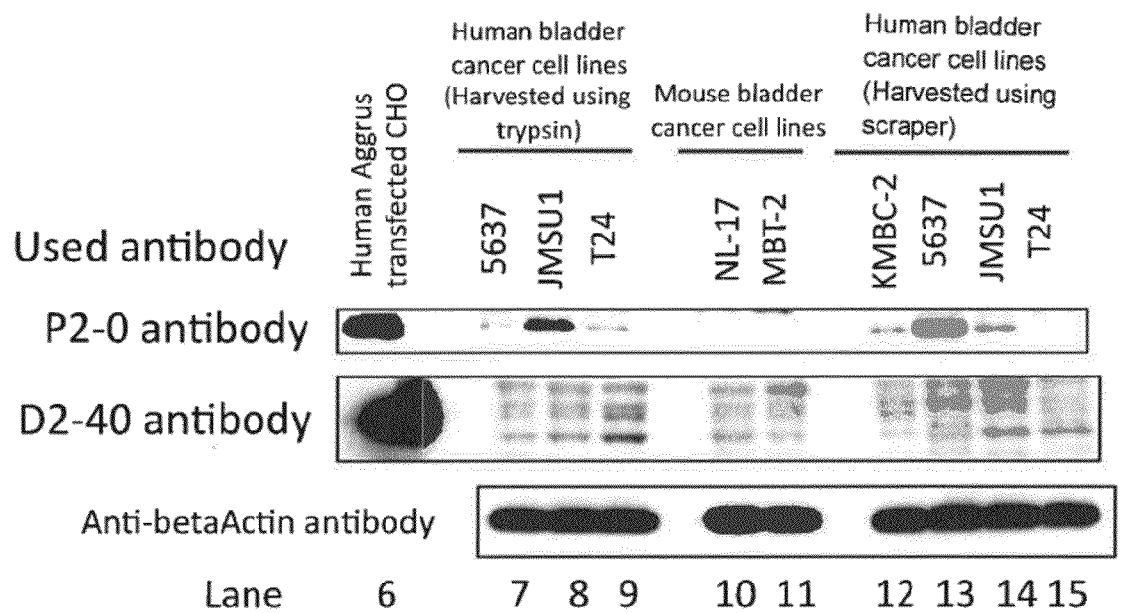
[FIG. 9]

Therefore, recognition of P2-0 mAb against Aggrus protein expressed in human bladder cancer cells were examined by western blotting. As shown in FIG. 8, P2-0 mAb recognized Aggrus protein (lane 2-5) expressed on membrane surface of each kind of human bladder cancer cells. On the other hand, purchased D2-40 antibody (mouse anti-human Aggrus mAb) only recognized CHO cells introduced with human Aggrus genes (lane 1), but not Aggrus expressed on membrane surface of human bladder cancer cells. Moreover, CHO cells introduced with human Aggrus genes and various human bladder cancer cell lines were harvested under the trypsinization which is a proteinase (FIG. 9; lane 7-9) or under no trypsinization (FIG. 9; lane 12-15), each cell lysate were performed with SDS-PAGE, and the western blotting was performed with P2-0 antibody, NZ-1 antibody and actin antibody to confirm amount of protein. As shown in FIG. 9, P2-0 mAb recognized Aggrus protein expressed on the membrane surface of human bladder cancer cells, but NZ-1 mAb could only recognize Aggrus expressed on CHO cells introduced with human Aggrus (FIG. 9: lane 6), so that it is apparent that NZ-1 mAb cannot recognize native Aggrus expressed on the membrane surface of human bladder cancer cells.

In this study, the reactivity of P2-0 mAb against native Aggrus protein expressed in living body is demonstrated to be higher, compared to that of anti-human Aggrus mAb (including NZ-1) that are known heretofore, indicating that P2-0 mAb is an antibody that could recognize Aggrus expressed in multiple types of cancers. Therefore, P2-0 mAb would possess much superior effects in Aggrus-targeting use.

Figure 10A:
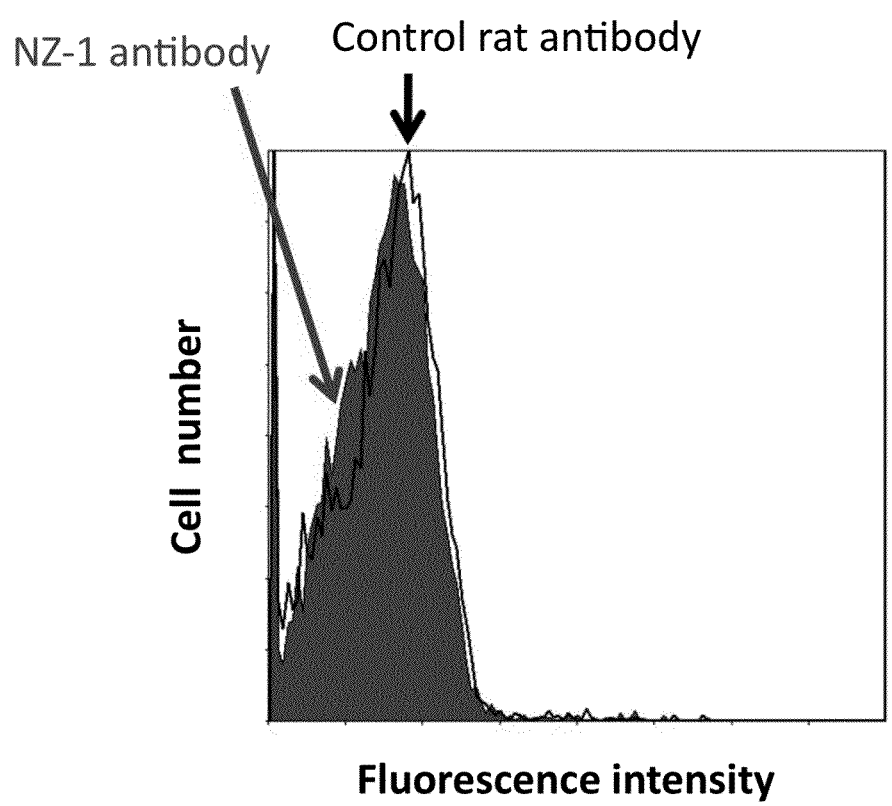
[FIG. 10A]

Furthermore, results of above-mentioned western blotting were confirmed by FACS analysis. Human bladder cancer T24 cells were harvested without trypsin, which is a proteinase, and cells were incubated with NZ-1 antibody or rat antibody which is a control antibody thereof for 1 hour at 4° C. After washing away the excessive antibodies with PBS, cells were incubated with Alexa fluor 488-labeled anti-rat IgG as a secondary antibody for 1 hour at 4° C. After washing away the excessive antibodies with PBS again, cells were analyzed by a Cytomics FC500 flow cytometry system (Beckman-Coulter). Results are shown in FIG. 10A.

Figure 10B:
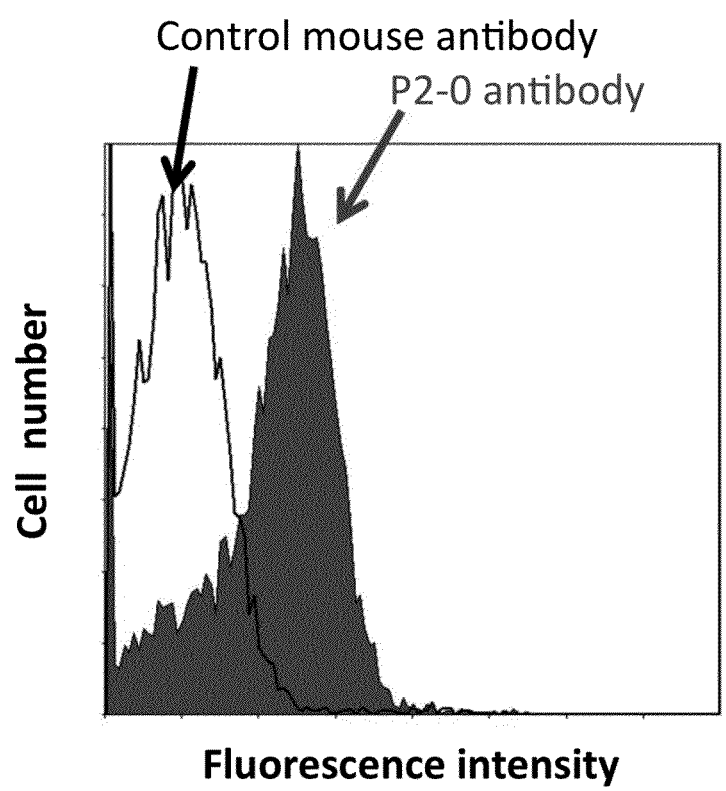
[FIG. 10B]

On the other hand, above-mentioned harvested T24 cells were incubated with P2-0 mAb or mouse antibody as the control antibody thereof for 1 hour at 4° C. After washing away the excessive antibodies with PBS, cells were incubated with Alexa fluor 488-labeled anti-mouse IgG for 1 hour at 4° C. After washing with PBS again, cells were analyzed by the flow cytometry system. Results are shown in FIG. 10B. As shown in FIGS. 10A and 10B, NZ-1 mAb did not recognize Aggrus expressed on human bladder cancer cells T24, but P2-0 mAb recognized the same.

Figure 11:
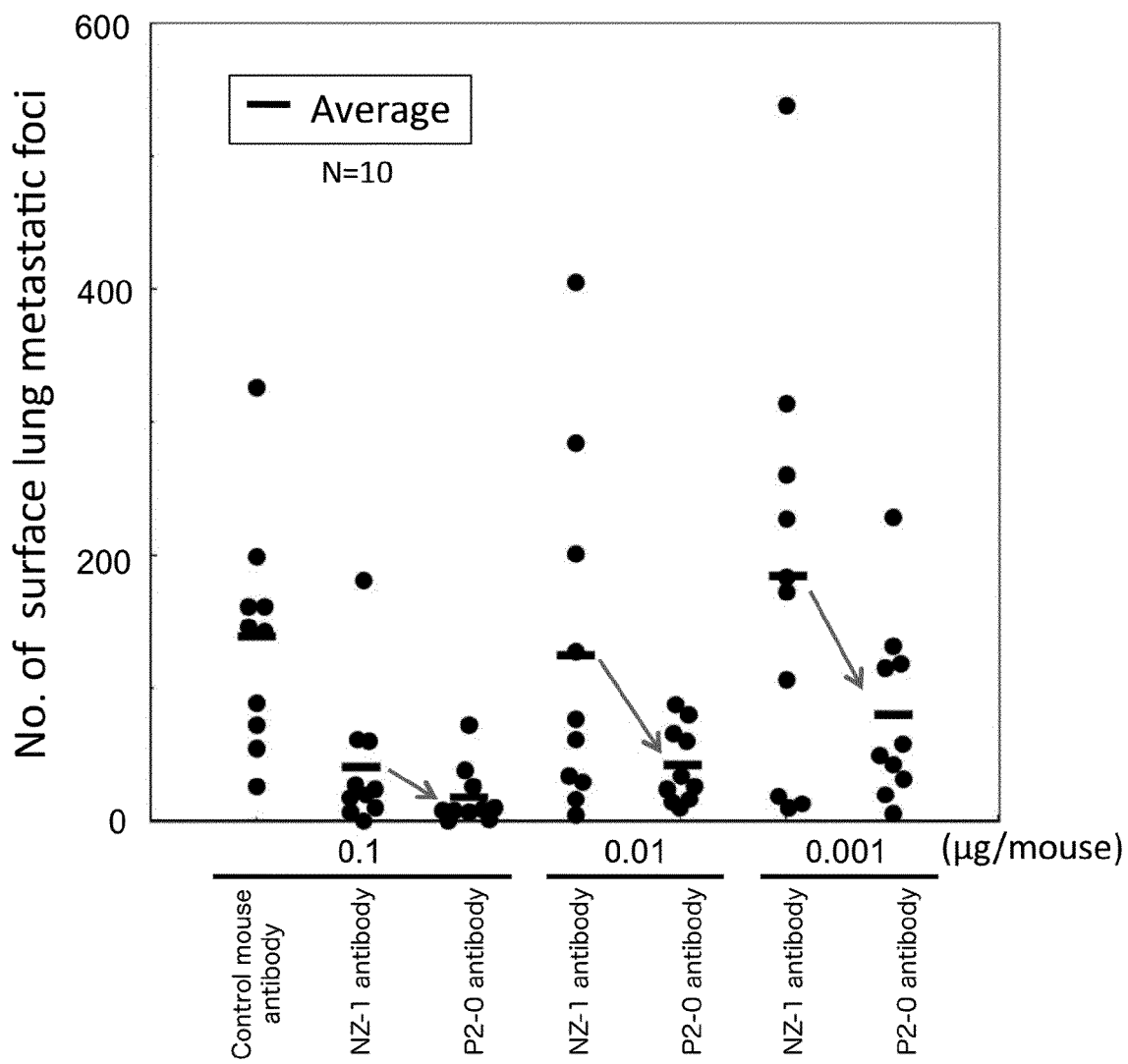
[FIG. 11]

The effects of P2-0 and NZ-1 mAbs on experimental pulmonary metastasis of CHO cells introduced with human Aggrus genes were examined in vivo. As shown in FIG. 11, administration of P2-0 mAb shows inhibitory effect on pulmonary metastasis compared to control antibody administration group with extremely small amount of 0.01 or 0.001 μg/mouse. It is apparent that, although administration of 0.1 μg/mouse of NZ-1 mAb inhibited the pulmonary metastasis, administration of small amount of 0.01 or 0.001 μg/mouse could not exhibit inhibitory activity significantly compared to the control antibody. These results indicated that P2-0 mAb is superior at recognition and functional inhibition of Aggrus and that P2-0 mAb possesses advantage in experimental and clinical use.

Embodiment 9

Immunogen to Establish Hybridomas which Produce Mouse Anti-Human Aggrus mAbs

A human aggrus cDNA region encoding the PP4626 antigen (21 a.a. located on 42-62, Sequence ID 5: Ala Met Pro Gly Ala Glu Asp Asp Val Val Thr Pro Gly Thr Ser Glu Asp Arg Tyr Lys Ser) was cloned and connected eighteen times repeatedly on a pGEX-6P-3 vector (GE Healthcare). BL21 *Escherichia coli* (Invitrogen) was transformed with these vectors, and GST-tagged recombinant proteins were purified using Glutathione Sepharose (GE Healthcare).

Sensitization

Six-week-old female BALB/c mice (bought from Charles River Laboratories Japan, Inc., and bred according to common procedure) were immunized by neck subcutaneous injections of the immunogen obtained above with TiterMax Gold (TiterMax USA, Inc). Every other week, intraperitoneal immunization was performed.

Establishment of Hybridomas

Spleen cells were obtained according to common procedure, and fused with mouse myeloma P3U1 cells using polyethylene glycol 4000 (Merck). Hybridoma cells were cultured and selected in S-Clone cloning medium (Eidia Co., Ltd.) containing hypoxanthine, aminopterin, and thymidine. As a result, a plurality of hybridomas were established.

Embodiment 10

Analysis of Mouse Anti-Human Aggrus mAbs Verification by Flow Cytometry

Figure 12A:
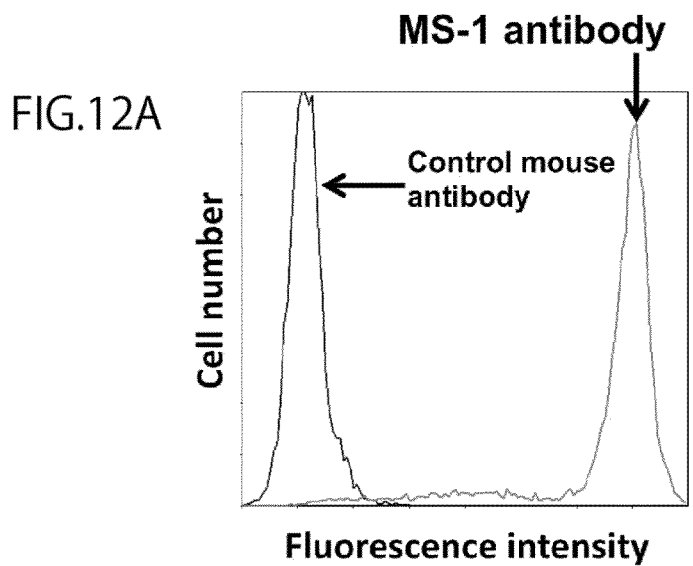
[FIG. 12A-12C]
Figure 12B:
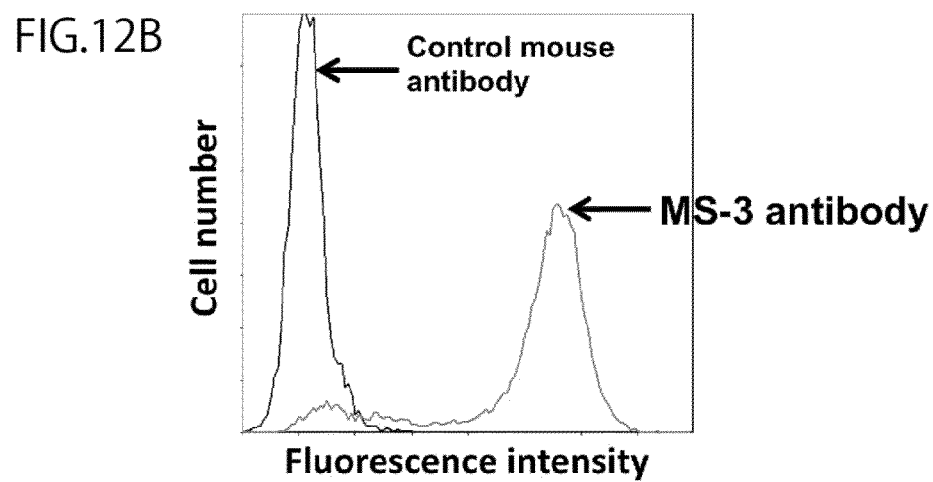
Figure 12C:
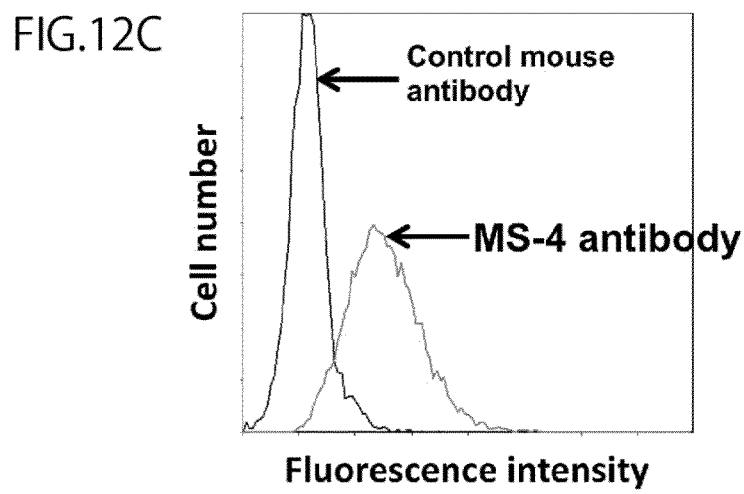
Figure 14A:
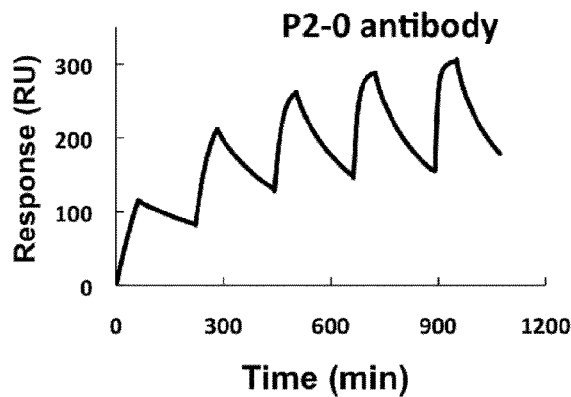
[FIG. 14A-14D]
Figure 14B:
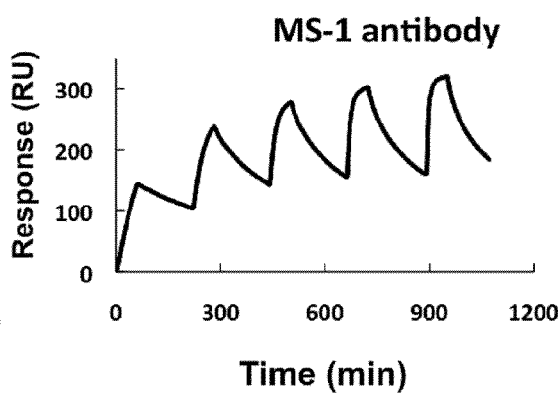
Figure 14C:
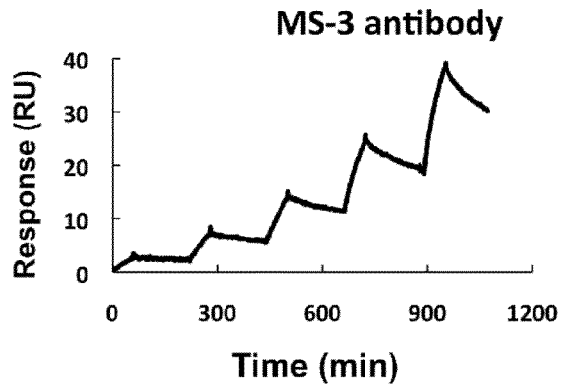
Figure 14D:
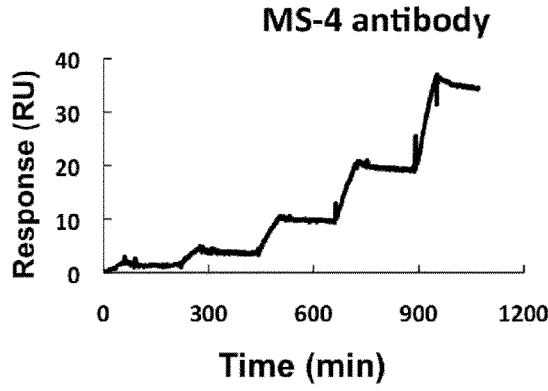

Among antibodies obtained from above-mentioned hybridomas, hybridomas which produces MS-1, MS-3, or MS-4 mAb were deposited to National Institute of Technology and Evaluation-International Patent Organism Depositary on Dec. 28, 2011 (assigned deposit IDs FERM BP-11447, FERM BP-11448, and FERM BP-11449 respectively). MS-1, MS-3, and MS-4 mAbs were confirmed to recognize human Aggrus by flow cytometry analysis using CHO cells introduced with human Aggrus gene. Specifically, CHO cells stably transfected with human Aggrus gene were collected from culture vessel, and after washing with PBS and adjusting to a cell concentration of $2 \times 10^6$ cells/ml, MS-1, MS-3, and MS-4 mAb were incubated for 30 min on ice. After washing the cells with PBS, cells were incubated with Alexa fluor 488-labeled anti-mouse IgG and reacted for 30 min on ice. After washing the cells three times with PBS, analysis was performed by a Cytomics FC500 (Beckman Coulter). The results are shown in FIG. 12.

Embodiment 11

Analysis of Epitope

By cloning human Aggrus cDNA removed with codon corresponding to signal peptide to pGEX-6P3 vector, and by replacing codon corresponding to $37^{th}$ to $62^{nd}$ amino acid with codon corresponding to alanine one by one using Quick-Change Site-Directed Mutagenesis Kit (Stratagene), various alanine variants of Aggrus expressed vector were prepared. *E. coli* TOP 10F' was transfected with each vector, and the homogenized sample was prepared after cultivation using these samples, western blotting was performed and analyzed reactivity of recombinant Aggrus protein to P2-0, MS-1, MS-3, and MS-4, respectively. As a result, as shown in upper panel of FIG. 13, P2-0 mAb showed high reactivity to $Gly^{45}$, $Asp^{48}$, and $Asp^{49}$ of human Aggrus protein, indicating that P2-0 mAb recognizes amino-acid sequence shown in Sequence ID 1. MS-1 mAb showed high reactivity to $Gly^{45}$ and $Asp^{48}$ of human Aggrus protein, indicating that MS-1 mAb recognizes amino-acid sequence shown in Sequence ID 1. MS-3 mAb showed high reactivity to $Gly^{54}$, $Thr^{55}$, and $Asp^{58}$ of human Aggrus protein, indicating that MS-3 mAb recognizes amino-acid sequence shown in Sequence ID 3. MS-4 mAb showed high reactivity to $Pro^{53}$, $Thr^{55}$, $Glu^{57}$, $Asp^{58}$, and $Lys^{61}$ of human Aggrus protein, indicating that MS-4 mAb recognizes amino-acid sequence shown in Sequence ID 4. Schematic view of recognition epitope of P2-0, MS-1, MS-3, and MS-4 antibodies are shown in lower panel of FIG. 13. Of the recognition epitope of human Aggrus primary sequence, amino acid shown in white bold letter are recognition sites of mAbs. Sites overlapped by ellipses show critical regions for antibody to recognize human Aggrus.

Embodiment 12

Binding Affinity of Antibodies to Recombinant Human Aggrus Protein Using Surface Plasmon Resonance Measurement of binding affinity to recombinant human Aggrus protein of P2-0, MS-1, MS-3 and MS-4 were performed using surface plasmon resonance analyzer Biacore X100 system (GE Healthcare, Buckinghamshire, UK). The recombinant Aggrus protein was covalently attached to a carboxymethyl dextran-coated CM5 sensor chip by the amine coupling method. Final levels of immobilization were about 2000 response units. All experiments were performed at 25° C. at a constant flow rate of 30 μl/min, with HBS-EP+ buffer (10 mM HEPES, 150 mM NaCl, 3 mM EDTA, 0.05% v/v Surfactant P20). P2-0, MS-1, MS-3, and MS-4 antibodies were diluted using HBS-EP+ buffer to 100 nM, 50 nM, 25 nM, 12.5 nM and 6.25 nM, respectively, were passed over the sensor chip CM5 with immobilized recombinant human Aggrus protein for 60 seconds to observe binding reaction, and the HBS-EP+ buffer alone was passed for 120 seconds to observe dissociation reaction. Sensorgrams obtained by the measurement were analyzed using the Biacore X100 evaluation software bivalent analyte model, and dissociation constant ($K_D$) was determined. As shown in FIG. 14, the dissociation constant of P2-0 with the recombinant human Aggrus protein was $9.3 \times 10^{-9}$ M, the dissociation constant of MS-1 was $9.0 \times 10^{-9}$ M, the dissociation constant of MS-3 was $6.3 \times 10^{-8}$ M, and the dissociation constant of MS-4 mAb was $2.0 \times 10^{-6}$ M, respectively.

Embodiment 13

Inhibition Assay of Aggrus-CLEC-2 Interaction

By using recombinant Aggrus and CLEC-2 proteins prepared from mammalian cells, Aggrus-CLEC-2 interaction was detected by ELISA method. Effects of anti-Aggrus mAbs against Aggrus-CLEC-2 interaction were examined. As shown in upper panel of FIG. 15, P2-0 and MS-1 mAbs inhibited Aggrus-CLEC-2 interaction in a concentration dependent manner. Moreover, as is shown in lower panel of FIG. 15, MS-3 and MS-4 mAbs inhibited Aggrus-CLEC-2 interaction in high concentration of 40 μg/mL or 80 μg/mL, respectively.

Embodiment 14

Inhibition Assay of Platelet Aggregation

It is known that when CHO cells incapable of inducing platelet aggregation is introduced with human Aggrus gene, the same induces platelet aggregation. In vitro platelet aggregation analysis was performed with monitoring of light transmittance with an MCM HEMA TRACER 313M (MC Medical), and the time from reaction-starting point until reaching 50% of maximum aggregation rate was compared. As shown in FIG. 16, platelet aggregation induced by the human Aggrus introduced CHO cells reach 50% aggregation rate after 2 to 3.5 minutes from reaction-starting point under presence of the control antibody (mouse IgG (PBS-dialyzed with catalogue No. 15381 of Sigma)), whereas the same was attenuated to 11 to 19 minutes after reaction-starting point under presence of P2-0 antibody. Further, the same attenuated to 9 minutes after reaction-starting point under presence of MS-1, attenuated to 14.5 minutes after reaction-starting point under presence of MS-3, and 10 minutes after reaction-starting point under presence of MS-4 antibodies. Therefore, it is shown that P2-0, MS-1, MS-3, and MS-4 mAbs have activity of inhibiting Aggrus-dependent platelet aggregation.

Embodiment 15

Antitumor Activity Assay

CHO cells introduced with human Aggrus gene was subcutaneously inoculated into the backs of twelve BALB/c-nu/nu nude mice at a cell number of $1\times10^5$ cells per mouse, and twelve mice was separated into two groups of six mice each. Setting the day cell transplantation was performed to Day 0, the control antibodies (mouse IgG2a (PBS-dialyzed with catalogue No. M9144 of Sigma)) and MS-1 antibodies to each group for three times on Day 1, Day 5 and Day 9. Administration amount of antibody was 30 µg/mouse, and the lateral tail vein was selected as an administration route. Tumor volume was measured twice in one week, and anti-tumor effect of MS-1 antibody was determined by measuring the same until 30 days after the subcutaneous inoculation. As shown in FIG. 17, growth of tumor is observed in five out of six mice in the control antibody treated group, and an average tumor volume of on day 30 was approximately 1,200 mm$^3$. On the other hand, tumors in two out of six mice were disappeared and tumors were reduced in three mice in the MS-1 antibody treated group, and the average tumor volume of on day 30 was 400 mm$^3$. These results indicated that MS-1 mAb exerts anti-tumor activity to human Aggrus expressed cells. Representative pictures of mice and tumor in Day 18 are shown in right panel of FIG. 17. The numbers 1 through 6 plotted to mice corresponded to those of each graph.

Embodiment 16

Spontaneous Metastasis Inhibitory Assay

When CHO cells introduced with human Aggrus are subcutaneously inoculated, it is known that the same show spontaneously lung metastasis after 30 days from transplantation. Therefore, lungs of tumor inoculated mice used in antitumor activity assay were enucleated 30 days after cell transplantation, was washed with PBS, was stained with saturated picric acid solution, and Lung surface metastatic foci were counted. A graph of the number of lung surface metastatic foci is shown in upper panel of FIG. 18. Representative pictures of the lungs of mice stained with picric acid are shown in lower panel of FIG. 18. Although about an average of 30 lung surface metastatic foci were observed in control antibody (mouse IgG2a (PBS dialyzed with catalogue No. M9144 of Sigma) treated group, MS-1 mAb treated group completely inhibited metastasis foci formation in five out of six mice. These results indicated that MS-1 mAb is an anti-Aggrus mAb that inhibits Aggrus-dependent spontaneous lung metastasis.

Embodiment 17

Pulmonary Metastasis Inhibitory Assay

Figure 19:
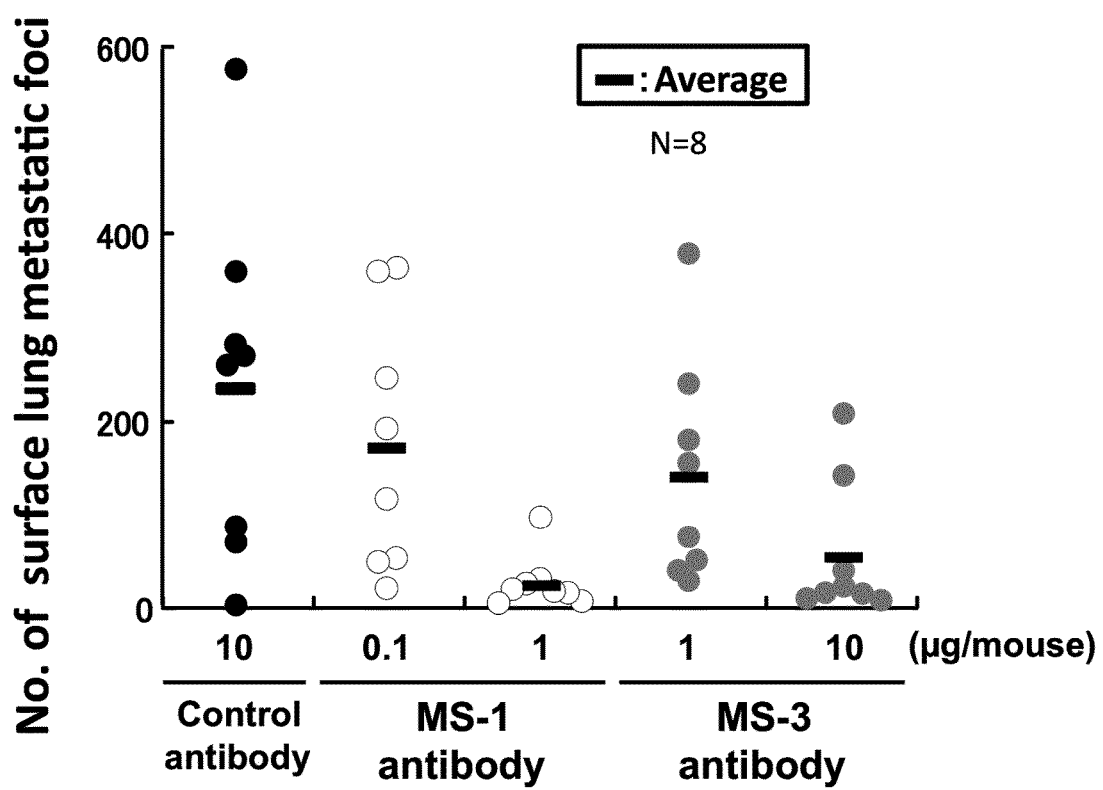
[FIG. 19]

It is known that when CHO cells introduced with human Aggrus is injected from the lateral tail vein of BALB/c-nu/nu nude mouse, lung metastatic foci are formed approximately 20 days from injection. As such, on a day before cell injection, the control antibody (mouse IgG2a (PBS dialyzed with catalogue No. M9144 of Sigma), MS-1 antibody and MS-3 antibody were administered via the lateral tail vein to eight nude mice each, and the influence on Aggrus-dependent experimental pulmonary metastasis were examined. As shown in FIG. 19, lung metastasis of Aggrus-introduced CHO cells was significantly suppressed by prior administration of MS-1 or MS-3 mAb in a concentration dependent manner. These results indicated that MS-1 and MS-3 mAb possess Aggrus-dependent pulmonary metastasis inhibitory activity as well as Aggrus neutralizing ability.

Deposit ID
FERM BP-11446
FERM BP-11447
FERM BP-11448
FERM BP-11449

---

The invention claimed is:

1. A mouse monoclonal antibody or a functional fragment thereof, which recognizes an Aggrus epitope consisting of an amino-acid sequence represented by a sequence ID 1, 3, or 4.

2. The monoclonal antibody or the functional fragment thereof according to claim 1, wherein the monoclonal antibody or the fragment is produced from a hybridoma having an IPDC-AIST Accession No. of FERM BP-11446, FERM BP-11447, FERM BP-11448 or FERM BP-11449.

3. The monoclonal antibody or the functional fragment thereof according to claim 1, wherein the monoclonal antibody or the fragment is humanized.

4. A hybridoma having an IPDC-AIST Accession No. of FERM BP-11446, FERM BP-11447, FERM BP-11448 or FERM BP-11449.

5. An Aggrus-CLEC-2 binding inhibitor consisting of the monoclonal antibody or the functional fragment thereof according to claim 1.

6. A composition containing the monoclonal antibody or the functional fragment thereof according to claim 1, for prevention of platelet aggregation, inhibition of cancer metastasis, or for treatment of tumor or thrombosis.

7. The composition according to claim 6, wherein the thrombosis is cerebral infarction or myocardial infarction.

8. The composition according to claim 6, wherein cancer or tumor is squamous cell carcinoma, fibrosarcoma, mesothelioma, Kaposi's sarcoma, testicular germ cell tumor, brain tumor, or bladder cancer.

9. The composition according to claim 8, wherein cancer or tumor is squamous cell carcinoma, mesothelioma, testicular germ cell tumor, or bladder cancer.

10. The monoclonal antibody or the functional fragment thereof according to claim 2, wherein the monoclonal antibody or the fragment is humanized.

11. The Aggrus-CLEC-2 binding inhibitor consisting of the monoclonal antibody or the functional fragment thereof according to claim 5, wherein the monoclonal antibody or the fragment is produced from a hybridoma having an IPDC-AIST Accession No. of FERM BP-11446, FERM BP-11447, FERM BP-11448 or FERM BP-11449.

12. The Aggrus-CLEC-2 binding inhibitor consisting of the monoclonal antibody or the functional fragment thereof according to claim 11, wherein the monoclonal antibody or the fragment is humanized.

13. A composition containing the monoclonal antibody or the functional fragment thereof according to claim 2, for prevention of platelet aggregation, inhibition of cancer metastasis, or for treatment of tumor or thrombosis.

14. A composition containing the monoclonal antibody or the functional fragment thereof according to claim 2, for prevention of platelet aggregation, inhibition of cancer metastasis, or for treatment of tumor or thrombosis.

\* \* \* \* \*